US007993917B2

(12) United States Patent
Martin

(10) Patent No.: US 7,993,917 B2
(45) Date of Patent: Aug. 9, 2011

(54) METHOD FOR OBTAINING A CELLULAR PRODUCT FROM A CELL OR A TISSUE USING PROTEIN-FREE MEDIUM

(75) Inventor: Samuel K. Martin, Nairobi (KE)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 12/544,733

(22) Filed: Aug. 20, 2009

(65) Prior Publication Data

US 2010/0092938 A1    Apr. 15, 2010

Related U.S. Application Data

(60) Division of application No. 11/150,322, filed on Jun. 13, 2005, now Pat. No. 7,611,896, which is a continuation-in-part of application No. 10/990,971, filed on Nov. 18, 2004, now Pat. No. 7,452,721, which is a continuation of application No. 10/173,586, filed on Jun. 18, 2002, now Pat. No. 7,008,774, which is a continuation of application No. 09/725,182, filed on Nov. 29, 2000, now abandoned.

(60) Provisional application No. 60/168,300, filed on Dec. 1, 1999.

(51) Int. Cl.
*C12N 1/10* (2006.01)
*C12N 1/20* (2006.01)
*C12N 5/00* (2006.01)
*C12N 5/02* (2006.01)
*C12P 1/00* (2006.01)

(52) U.S. Cl. .......... 435/374; 435/41; 435/373; 435/375; 435/382; 435/383; 435/384; 435/385; 435/388; 435/390; 435/391; 435/392; 435/404; 435/407; 435/253.6; 435/255.21; 435/258.3

(58) Field of Classification Search ........................ None
See application file for complete search history.

(56) References Cited

U.S. PATENT DOCUMENTS 5,888,815 A * 3/1999 Nilsson et al. ................ 435/360
2003/0008332 A1   1/2003 Ryan

OTHER PUBLICATIONS

Cheung et al., (J. of Surgical Research. 1996. vol. 66:81-89).*
Chang et al., (1992. Development. vol. 114:509-519).*
Kozka et al., (1991. J. of Biological Chem. vol. 266(18): 11,726-11,731).*

(Continued)

*Primary Examiner* — Albert Navarro
*Assistant Examiner* — J. Hines
(74) *Attorney, Agent, or Firm* — Elizabeth Arwine

(57) ABSTRACT

Methods for the diagnosis of visceral, cutaneous and canine leishmaniasis in a subject suspected of being infected with the parasitic protozoa *Leishmania* is disclosed. Disclosed are antibody-capture enzyme-linked immunosorbent assays (ELISAs) for the detection of antibodies to *Leishmania* parasite soluble antigens and antigen-capture ELISAs for the detection of *Leishmania* parasite soluble antigens in host samples. Also disclosed are immunodiagnostic kits for the detection of *Leishmania* parasite circulating antigens or IgM and IgG antibodies in a sample from subject having visceral, cutaneous or canine leishmaniasis. In these methods and kits, detection may be done photometrically or visually. The methods and kits also allow the visualization of *Leishmania* amastigotes or promastigotes in a sample.

20 Claims, 11 Drawing Sheets

OTHER PUBLICATIONS

Martin et al., (Jun. 1998 Annals of tropical Medicine and Parasitology. vol. 92(5):571-577).*

Mbui et al. (1999. East African Medical Journal, Letters to the Editor in Chief. p. 358).*

Limoncu et al. (2004) "Evaluation of three new culture media for the cultivation and isolation of Leishmania parasites" J. Basic Microbiol. 44(3):197-202.

Mukerji et al. (1991) "Direct Enzyme-Linked Immunosorbent Assay: A Simple Immunoassay Using *Leishmania donovani* Promastigote for Diagnosis of Kala-Azar" J. Clin Lab. Anal. 5:299-301.

International Search Report and Written Opinion in PCT/US00/032523 dated Jun. 27, 2001.

International Search Report and Written Opinion in PCT/US2006/022839 dated Nov. 26, 2007.

R. Badario, D. Benson, M.C. Eulallo, M. Freire, S. Cunha, E.M. Netto, D. Pedral-Sampalo, C. Madureira, J. M. Burns, R. L. Houghton, J. R. David, and S. G. Reed rK39: A Cloned Antigen of *Leishmania chagasi* that Predicts Active Visceral, JID, 1996, 173:758-761.

R. Badaro, S. Reed, A. Barral, G. Orge, and T. Jones, Evaluation of the Micro Enzyme-Linked Immunosorbent Assay (Elisa) for Antibodies in Selection for Detection of Infection-Specific Responses, Am. J. Trop. Med. Hyg., 1986, 35(1) 72-78.

P. A. Bates, M. Kurtz, M. Gottlieb, and D. M. Dwyer, *Leishmania donovant*: Generation of Monospecific Antibody Regents to Soluble Acid Phosphatase, Experimental Parasitology 1987, 64:157-164.

P. A. Bates M. Gottlieb, and D. M. Dwyer, *Leishmania donovani*: Identification of Glycoproteins Released by Promastigotes during Growth in Vitro, Experimental Parasitology, 1988, 67:199-209.

R. S. Bray and R. Lainson, The Immunology and Serology of Leishmanisis IV. Results of Ouchterlony Double Diffusion Tests, Transactions of the Royal society of Tropical Medicine and Hygiene, 60(5) 1966.

A. Choudhry, P. Y. Guru, R. P. Saxena, A. Tandon, and K. C. Saxena, Enzyme-linked immunosorbent assay in the Diagnosisi of Kala-Azar in Bhodohi (Varanasl), India, Transactions of the Royal Society of Tropical Medicine and Hygiene, 1990 84:363-366.

A. Choudhry, A. Puri, P. Y. Guru, R. P. Sexena, and K. C. Saxena, An Indirect Fluorescent Antibody (IFA) Test for the Serodiagnosis of Kala-Azar, J. Com. Dis., 1992, 24(1):32-36.

S. L. Ellis, A. M. Shankarian, and D. M. Dwyer, *Leishmania*: Amastigotes Synthesize Conserved Secretory Acid Phosphates during Human Infection, Experimental Parasitology, 1998, 89:161-168.

J. El-On, L. F. Schnur, and C. L. Greenblatt, *Leishmania donovani*: Physicochemical, Immunological, and Biological Characterization of Excreted Factor from Promastigotes, Experimental Parasitology, 1979, 47:254-269.

M. del R. Garcia-Miss, F. J. Andrade-Narvaez, R. E. Esquivel-Vinas, E. B. Simmonds-Diaz, B. Canto-Lara, and L. Cruz-Ruiz, Transactions of the Royal Society of Tropical Medicine and Hygiene, 1990, 84:356-358.

K. D. Greis, and S. J. Turco, Purification and Characterization of an Extracellular Phosphoglycan from *Leishmania donovani*, The Journal of Biological Chemistry, Mar. 25, 1992, 267(9):5876-5881.

S. K. Martin, L. Thuita-Harun, M. Adoyo-Adoyo and K. M. Wasunna; A Diagnostic ELISA for Visceral Leishmaniasis, based on Antigen form Media Conditioned by *Leishmania donovani* promastigotes, Annals of Tropical Med. & Parasitology, 1998 92(5):571-577.

S. G. Reed, W. G. Shreffler, J. M. Burns, Jr., J. M. Scott, M. G. Orge, H. W. Ghalib, M. Siddig, and R. Badaro, An Improved Serodiagnostic Procedure for Visceral Leishmaniasis, Am. J. Trop. Med. Hyg., 1990, 43(6):632-639.

J. L. Sanchez, B. M. Diniega, J. W. Small, R. N. Miller, J. M. Andujar, P. J. Weina, P. G. Lawyer, W. R. Ballou and J. K. Lovelace, Am. J. Rtop Med. Hyg., 1992, 47(1):47-54.

L. F. Schnur, M.sc., A. Zuckerman, Ph.D., and C. L. Greenblatt, M.D., Leishmanial Serotypes as Distinguished by the Gel Diffusion of Factors Excreted In Vitro and In Vivo, Isrl. J. Med. Sci., 1972, 8(7):932-942.

G. Senaldi, H. Xio-su, D.C. Hoessil, C. Bordler, Serological Diagnosis of Visceral Leishmaniasis by a Dot-enzyme Immunoassay for the Detection of a *Leishmania donovani*-related Circulating Antigen, Journal of Immunological Methods, 1996, 193:9-15.

Sergeiev, V. P., et al., Med. Parasitol., 1995, 38:208-212.

E. E. Zijlstra, O. F. Osman, H. W. Chr. Hofland, L. Oskam, H. W. Ghalib, A. M. El-Hassan, P. A. Hager, and S. E. O. Meredith, Transactions of the Royal Society of Tropical Medicine and Hygiene, 1997 91:671-673.

* cited by examiner

Figure 7: Western blot showing specific activity of Rabbit anti-leishmania PAb, normal human sera and sera from kala azar patients.

METHOD FOR OBTAINING A CELLULAR PRODUCT FROM A CELL OR A TISSUE USING PROTEIN-FREE MEDIUM

CROSS REFERENCE TO RELATED APPLICATIONS

This application is divisional of U.S. patent application Ser. No. 11/150,322, filed 13 Jun. 2005, used as U.S. Pat. No. 7,611,896, which is a continuation-in-part of U.S. patent application Ser. No. 10/990,971, filed 18 Nov. 2004, issued as U.S. Pat. No. 7,452,721, which is a continuation of U.S. patent application Ser. No. 10/173,586, filed 18 Jun. 2002, issued as U.S. Pat. No. 7,008,774, which is a continuation of U.S. patent application Ser. No. 09/725,182, filed 29 Nov. 2000, now abandoned, which claims the benefit of U.S. Provisional Patent Application No. 60/168,300, filed 1 Dec. 1999, all of which are herein incorporated by reference.

ACKNOWLEDGMENT OF GOVERNMENT SUPPORT

This invention was made by employees of the United States Army. The government has rights in the invention.

BACKGROUND OF THE INVENTION

1. Field of the Invention

This invention relates generally to a method of diagnosing leishmaniasis in a subject suspected of being infected with the parasitic protozoa *Leishmania*. In particular, the invention relates to enzyme-linked immunosorbent assays (ELISAs) for the detection of *Leishmania* parasite circulating antigens and *Leishmania*-specific antibodies in host samples.

2. Description of the Related Art

Leishmaniasis is a serious and sometimes fatal disease estimated by the World Health Organization (WHO) to affect approximately 12 million people in 88 countries. Recent epidemics of leishmaniasis have occurred in the Africa, the Indian subcontinent and Brazil. The significant morbidity and mortality caused by leishmaniasis is a cause for concern in endemic areas. Such concern has more recently expanded to include non-endemic areas because of the increase in global travel concomitant with the increased incidence of the disease in HIV-infected and intravenous drug-user populations.

Unfortunately, current acceptable diagnostic practices lack the means for efficiently and accurately identifying those infected or exposed to the disease-causing parasite as explained in Martin, S. et al. (1998) Military Medicine 163 (23):801-807. As a result, the prevention of leishmanial epidemics is greatly hindered and patient management is difficult. Additionally, there is an imminent threat of HIV and *Leishmania* co-infection, a more malignant infection that is difficult to diagnose and treat. To date, there are no antigen-detection type diagnostic tests available for leishmaniasis. In view of this, antigen-detection assays are desperately needed for diagnosis, patient management and epidemiological studies.

Recombinant kinesin protein, rK39, is one of the few antigens that have been used in the development of antibody-detection immunoassays for active visceral leishmaniasis (VL). However, assays developed with this antigen and others fail to consistently detect antibodies in other clinical syndromes associated with a predominately T-cell and muted B-cell response. Moreover, antibody-detection assays have an inherent dependence on the immune response of the host to the parasite antigen which significantly diminishes its use. For example, in HIV/AIDS and other immuno-compromised conditions, the infection may not produce proportional antibody production and thereby escape detection.

Generally, the serological tests for diagnosing active VL are highly sensitive (>90%). See Senaldi, G., et al., (1996) J. Immunol. Methods 193:9-5. These serological tests, however, pose problems of non-specificity resulting in false positive results from reference samples of other infectious diseases. Modifications of the antigens used for direct agglutination test (DAT) and for ELISA in eliminating false-positive results have met variably success. See Zijlstra, E. E., et al., (1997) Trans. R. Soc. Trop. Med. Hyg. 91:671-673 and Badaro, R., et al., (1996) J. Inf. Dis. 173:758-761. Unfortunately, serological tests are rarely performed to diagnose cutaneous leishmaniasis, the most common form of the disease, because the sensitivities and specificities are disappointingly low for this clinical manifestation. See Sanchez, J. L., et al., (1992) Am. J. Trop. Med. Hyg. 47:47-54; Garcia-Miss, M. R., et al., (1990) Trans. R. Soc. Trop. Med. Hg. 84:356-358.

The antigens used in immunoassays for the detection of leishmaniasis are traditionally derived from promastigotes cultivated in vitro, or from recombinant proteins. See Badaro et al. (1996); Choudhary, S., et al., (1992) J. Comm. Dis. 24:32-36; Badaro, R., et al., (1986) Am. J. Trop. Med. Hyg. 35:72-78; Choudhary, A., et al., (1990) Trans. R. Soc. Trop. Med. Hyg. 84:363-366; and Reed, S. G., et al., (1990) Am. J. Trop. Med. Hyg. 43:632-639. However, promastigotes shed, excrete and secrete products into the culture medium to produce conditioned medium. These released products or exo-antigens are immunogenic to the host. See Schnur, L. F., et al., (1972) Isrl. J. Med. Sci. 8:932-942; Sergeiev, V. P., et al., (1969) Med. Parasitol. 38:208-212; El-On, J., et al., (1979) Exper. Parasitol. 47:254-269; and Bray, R. S., et al., (1966) Trans. R. Soc. Trop. Med. Hyg. 60:605-609.

In the prior art assays these exo-antigens are released into in vitro culture medium containing serum. Thus, the presence of complex proteins or serum components required for growth of the parasites in the culture medium pose several problems in the prior art assays. For example, the amount of manipulation needed to purify the targeted antigens from spent media can affect the native composition of certain components necessary for a highly sensitive assay. Furthermore, insufficient purification of parasite products may create problems with specificity as serum proteins contaminants in the antigen preparations, cause non-specific downstream reactions. Generally, the prior art assays are limited in scope to one species complex or clinical manifestation and have never demonstrated combined sensitivity and specificity of more than 90%.

Thus, a need exists for highly sensitive and highly specific assays for screening for exposure or diagnosing *Leishmania* infections.

SUMMARY OF THE INVENTION

The invention relates to an immunoassay for detecting IgM and IgG antibodies in a sample from a subject having visceral, cutaneous or canine leishmaniasis.

The invention also relates to an immunoassay for detecting *Leishmania* parasite circulating antigens in a sample from a subject having visceral, cutaneous or canine leishmaniasis.

In one embodiment, the invention relates to a leishmaniasis immunoassay, which is based on soluble antigens from promastigotes cultivated in a protein-free and serum-free medium.

In another embodiment, the invention relates to the use of protein-free and serum-free medium to cultivate the promastigotes in an immunoassay for the diagnosis of leishmaniasis.

In a preferred embodiment, the assay of the invention has a high degree of sensitivity and specificity. For example, the assay of the invention has a combined sensitivity and specificity of more than about 90%. Preferably, the assay of the present invention has sensitivity of about 95.1% and a specificity of about 100%.

The invention also relates to an antigen-capture immunoassay for the detection of exo-antigens released by the parasite in a serum sample from subjects having visceral, cutaneous or canine leishmaniasis.

The invention also relates to immunodiagnostic kits for the detection of specific IgM and IgG antibodies to *Leishmania* parasite circulating antigens in a sample from a subjects having visceral, cutaneous or canine leishmaniasis. Detection may be done photometrically or visually. If visual detection is desired, a fluorescent, chromogenic or chemiluminescent agent may be utilized. Preferably, the intensity or amount of the visual signal is in proportion to the amount of the antibody present in the sample.

In one embodiment, the invention allows for the visualization of *Leishmania* amastigotes or promastigotes by the use of a fluorescein conjugated polyclonal antibody to the specific antigen preparation aforementioned.

Preferably, the protein-free and serum-free medium utilized in the present invention comprises an oncotic agent that is not metabolized by cells in culture and is relatively easy to separate from proteins by dialysis. In a preferred embodiment of the invention, the medium comprises xylose as xylose is not metabolized by animal cells and parasites in cultures. Additionally, xylose is a low molecular weight compound and only small amounts are required. Since xylose is a small dialyzable molecule, purification is relatively easy and less destructive to the exo-antigen components found in the conditioned medium.

The present invention provides a method of maintaining or modulating water homeostasis in a cell or a tissue ex vivo comprising cultivating the cell or the tissue in a protein free medium containing an oncotic agent. In some embodiments, the oncotic agent is sucrose, ficoll, sorbitol or D-xylose. In some embodiments, the protein free medium further comprises RPMI Medium 1640, Hepes buffer, L-glutamine, and sodium bicarbonate without phenol red. In some embodiments, the protein free medium is RPMI Medium 1640 comprising D-xylose at 0.076 mM, Hepes buffer at 25 mM, L-glutamine, and sodium bicarbonate at 30 mM without phenol red. In some embodiments, the protein free medium is RPMI Medium 1640 comprising D-xylose at 0.076 mM, Hepes buffer at 25 mM, L-glutamine, sodium bicarbonate at 30 mM without phenol red, and 300 mg/dl D-glucose. In some embodiments, the protein free medium is RPMI Medium 1640 comprising D-sucrose at 0.076 mM, Hepes buffer at 25 mM, L-glutamine, sodium bicarbonate at 30 mM without phenol red, and 300 mg/dl D-glucose. In some embodiments, the protein free medium is RPMI Medium 1640 comprising D-ficoll at 0.076 mM, Hepes buffer at 25 mM, L-glutamine, sodium bicarbonate at 30 mM without phenol red, and 300 mg/dl D-glucose. In some embodiments, the protein free medium is RPMI Medium 1640 comprising D-sorbitol at 0.076 mM, Hepes buffer at 25 mM, L-glutamine, sodium bicarbonate at 30 mM without phenol red, and 300 mg/dl D-glucose. In some preferred embodiments, the protein free medium is SUM, FIM, SOM, XOM, or GFXOM. In some embodiments, the cell is a hybridoma, a beta-islet cell, a lymphocyte, a monocyte, a macrophage, a fibroblast, a stem cell, an endothelial cell, or the like. In some embodiments, the tissue is pancreatic, liver, heart, brain, kidney tissue, or the like. In some embodiments, the cell is not a *Plasmodium* or a *Leishmania* parasite.

In some embodiments, the present invention provides a method of obtaining a cellular product from a cell or a tissue comprising cultivating the cell or the tissue in a protein free medium containing an oncotic agent. In some embodiments, the oncotic agent is sucrose, ficoll, sorbitol or D-xylose. In some embodiments, the protein free medium further comprises RPMI Medium 1640, Hepes buffer, L-glutamine, and sodium bicarbonate without phenol red. In some embodiments, the protein free medium is RPMI Medium 1640 comprising D-xylose at 0.076 mM, Hepes buffer at 25 mM, L-glutamine, and sodium bicarbonate at 30 mM without phenol red. In some embodiments, the protein free medium is RPMI Medium 1640 comprising D-xylose at 0.076 mM, Hepes buffer at 25 mM, L-glutamine, sodium bicarbonate at 30 mM without phenol red, and 300 mg/dl D-glucose. In some embodiments, the protein free medium is RPMI Medium 1640 comprising D-sucrose at 0.076 mM, Hepes buffer at 25 mM, L-glutamine, sodium bicarbonate at 30 mM without phenol red, and 300 mg/dl D-glucose. In some embodiments, the protein free medium is RPMI Medium 1640 comprising D-ficoll at 0.076 mM, Hepes buffer at 25 mM, L-glutamine, sodium bicarbonate at 30 mM without phenol red, and 300 mg/dl D-glucose. In some embodiments, the protein free medium is RPMI Medium 1640 comprising D-sorbitol at 0.076 mM, Hepes buffer at 25 mM, L-glutamine, sodium bicarbonate at 30 mM without phenol red, and 300 mg/dl D-glucose. In some preferred embodiments, the protein free medium is SUM, FIM, SOM, XOM, or GFXOM. In some embodiments, the cellular product is secreted by the cell into the protein free medium. In some embodiments, the cell is a hybridoma, a beta-islet cell, a lymphocyte, a monocyte, a macrophage, a fibroblast, a stem cell, an endothelial cell, or the like. In some embodiments, the tissue is pancreatic, liver, heart, brain, kidney tissue, or the like. In some embodiments, the cell is not a *Plasmodium* or a *Leishmania* parasite.

In some embodiments, the present invention provides a method of cultivating, preserving or storing an organism, a cell, a tissue or organ comprising placing the organism, the cell, the tissue or organ in a protein free medium containing an oncotic agent. In some embodiments, the oncotic agent is sucrose, ficoll, sorbitol or D-xylose. In some embodiments, the protein free medium further comprises RPMI Medium 1640, Hepes buffer, L-glutamine, and sodium bicarbonate without phenol red. In some embodiments, the protein free medium is RPMI Medium 1640 comprising D-xylose at 0.076 mM, Hepes buffer at 25 mM, L-glutamine, and sodium bicarbonate at 30 mM without phenol red. In some embodiments, the protein free medium is RPMI Medium 1640 comprising D-xylose at 0.076 mM, Hepes buffer at 25 mM, L-glutamine, sodium bicarbonate at 30 mM without phenol red, and 300 mg/dl D-glucose. In some embodiments, the protein free medium is RPMI Medium 1640 comprising D-sucrose at 0.076 mM, Hepes buffer at 25 mM, L-glutamine, sodium bicarbonate at 30 mM without phenol red, and 300 mg/dl D-glucose. In some embodiments, the protein free medium is RPMI Medium 1640 comprising D-ficoll at 0.076 mM, Hepes buffer at 25 mM, L-glutamine, sodium bicarbonate at 30 mM without phenol red, and 300 mg/dl D-glucose. In some embodiments, the protein free medium is RPMI Medium 1640 comprising D-sorbitol at 0.076mM, Hepes buffer at 25 mM, L-glutamine, sodium bicarbonate at 30 mM without phenol red, and 300 mg/dl D-glucose. In some preferred embodiments, the protein free medium is SUM, FIM, SOM, XOM, or GFXOM. In some embodiments, the cell is a hybridoma, a beta-islet cell, a lymphocyte, a monocyte, a macrophage, a fibroblast, a stem cell, an endothelial cell, or the like. In some embodiments, the tissue is pancreatic, liver, heart, brain, kidney tissue, or the like. In some embodiments, the organism is a barophylic cell or organism. In some embodiments, the cell or organism is not a *Plasmodium* or a *Leishmania* parasite.

DESCRIPTION OF THE DRAWINGS

This invention is further understood by reference to the drawings wherein.

DETAILED DESCRIPTION OF THE INVENTION

Figure 1:
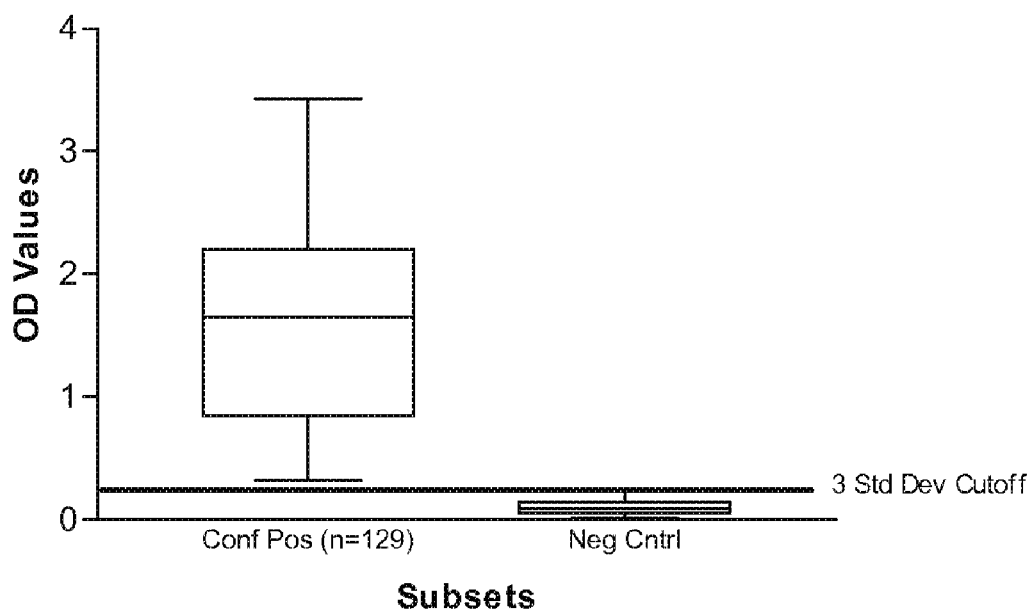
FIG. 1 is a boxplot to illustrate specific IgG antibody levels measured in VL patient sera samples.

Recently, the soluble antigens shed, excreted and secreted by *Leishmania* parasites in a protein-free medium have been described. The soluble antigens of *L. donovani* promastigotes, are primarily lipophosphoglycan (LPG), and comprise an albumin binding site, a hydrophylic LPG component, and a repeating phosphorylated saccharide linked with secreted acid phosphatase (S-AcP). See Greis, K. D., et al., (1992) J. Biol. Chem. 267:5876-5881. S-AcP is presumably the most immunogenic of all the glycoproteins and is a major component in *L. donovani* promastigote conditioned medium. See Bates, P. A., et al., (1988) Exper. Parasitol. 67:199-209. Monoclonal antibody (MAb) studies show no cross reactivity between S-AcP and parasite surface membrane or host acid phosphatases. See Bates, P. A., et al., (1987) Exper. Parasitol. 64:157-164. S-AcP from *L. donovani* promastigote conditioned medium has been used to immunoprecipitate specific antibody from pooled sera of patients acutely ill with VL (kala-azar). See Ellis, S. L., et al., (1998) Exp. Parasitol. 89:161-168.

The use of a soluble antigen preparation from *Leishmania donovani* to capture specific IgG antibodies in the sera of kala-azar patients indicates that the soluble antigens found in conditioned medium can act as the foundation for developing improved leishmaniasis immunoassays. See Martin et al. (1998) An. Trop. Med. & Parasit. 92: 571-577.

Thus, the present invention generally relates to leishmaniasis immunoassays, which are highly sensitive and specific and allow the detection of specific IgG and IgM antibodies in subjects affected with visceral, cutaneous, or canine leishmaniasis. The present invention also relates to antigen-capture immunoassays which allow the detection of the soluble *Leishmania* antigens.

The present invention relates to an immunoassay that allows the detection of IgM and IgG antibodies in subjects affected with visceral, cutaneous, or canine leishmaniasis. The assay is based on soluble antigens from promastigotes cultivated in a protein-free and serum-free medium and takes less than four hours to perform.

Prior research attempts employing non-recombinant antigens in the design of serologic tests for leishmaniasis have been limited by problems with sensitivity, specificity and test reproducibility. Reasons for these limitations remain elusive, but are most likely attributable to physical and chemical techniques used in antigen preparation. Therefore, the present invention relates to sensitizing plates with soluble antigens from conditioned media. Plate sensitization with antigen procured in protein-free medium ameliorates the prior art problems associated with physical and chemical techniques used in antigen preparation.

In order to obtain soluble antigens from conditioned media, cells must be maintained within defined physiological ranges to thrive in vitro. These conditions include temperature, pH, osmotic pressure, $O_2$ and $CO_2$ gas tension, and nutrients. It has been shown that cells fail to thrive in culture media unless 10 to 20% serum albumin is added and the viability and growth rates are compromised where serum albumin concentrations vary substantially from 10%. It is believed that the primary role of serum albumin in in vivo and in vitro cell culture systems is to balance oncotic pressure across the semi-permeable membrane of cells and to provide free water homeostasis. It is also believed that a critical component of serum for in vitro cell survival is albumin.

Therefore, one aspect of the present invention is the propagation of the promastigotes in serum-free and protein-free medium comprising an agent that balances the oncotic pressure across the semi-permeable membrane of the cells. An example of this agent is xylose. Thus, the uncharacterized soluble factors in conditioned medium from the cultivation of promastigotes in protein-free medium can be used as a foundation for an immunoassay for visceral, cutaneous, or canine leishmaniasis. The use of a defined protein-free culture medium reduces antigen production to a simple and inexpensive centrifugation step and greatly increases the sensitivity, specificity, reproducibility and practicability of the assay. Additionally, gram quantities of the soluble antigens may be inexpensively and reproducibly generated by methods standard in the art. Furthermore, reactivity to the soluble antigens appears to be genus specific.

Since sensitivity to oncotic imbalance varies with cell type, one may wish to conduct experiments to determine the optimum concentration range of the agent which balances the oncotic pressure across the semi-permeable membrane of a given cell type. For example, parasites may be cultured in a protein-free medium, wherein a colloidal agent balances the oncotic pressure. The growth index may be determined by comparing the growth of the parasites in the serum-free and protein-free medium with the growth of the parasites in serum supplemented media. Based on the comparison, one may then choose the optimum concentration range of the colloidal agent.

When attempting to detect specific IgM, normally one must consider the effect of IgG in the sample and compensate for its presence or eliminate it altogether. Thus, a fraction of samples tested (n=100) were subjected to a Rapi-Sep spin column (INDX), which binds the IgG in the samples to the membranes, before testing for specific IgM. There was no significant change in the IgM values derived for any of the treated samples.

In preliminary studies, 129 visceral (Brazil, Italy, North Africa, Nepal) and 143 cutaneous (Brazil) leishmaniasis patients with controls were tested. These studies show an overall sensitivity of 95.1% when *Leishmania*-specific IgG was measured against that of healthy, North American negative controls. No cross-reactivity was noted when this assay was used to look for cross-reacting antibodies in patient samples from other parasitic diseases (malaria, echinococcosis, Africa trypanosomiasis, and filariasis). See Martin et al.

Figure 2:
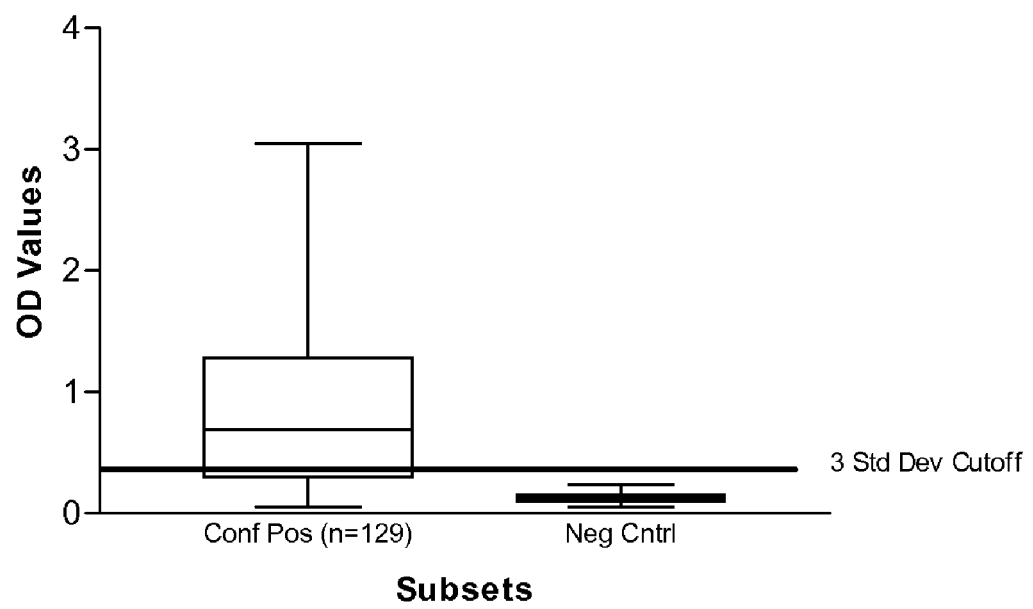
FIG. 2 is a boxplot showing specific IgM antibody levels measured in the same samples.

In additional studies, the assay of the present invention correctly identified 42 sera from Brazilian dogs with canine leishmaniasis and 10 healthy controls. As shown in FIGS. 1-6, the difference between negative and positive was greater in the case of dog sera than of human sera. The negative control sera subset gave a negative cutoff score of about 0.225 for the IgG assay. FIG. 1 is a boxplot to illustrate specific IgG antibody levels measured in VL patient sera samples. With respect to specific IgG, all 129 clinically confirmed positive VL patient sera gave OD readings above the negative cutoff (100% sensitivity). FIG. 2 is a boxplot showing specific IgM antibody levels measured in the same samples. When measuring IgM, the negative control sera tested gave a negative cutoff score of about 0.310. The sensitivity for this assay was 94.57% (122/129 positive).

Currently, the assay is able to detect specific IgG and IgM antibodies with varying degrees of success in patient serum samples from known-positive cases of visceral leishmaniasis (VL) and cutaneous leishmaniasis (CL). The assay may be improved by modifying serum sample and conjugate dilution, substrate, incubation times, temperatures, and other assay conditions, such as described in Example 8, and is well within the skill and knowledge of one of ordinary skill in the art. For example, the serum may be diluted by 1:1000 instead of 1:200 and all incubations may be at room temperature instead of a 37° C. humidity chamber. Serum samples may be diluted from about 1:250 to about 1:1,000. Preferably, for CL assays, the serum sample is diluted to 1:250 and for VL assays, the serum sample is diluted to 1:1,000. The wide range of conjugates that may be produced from polyclonal antibodies against these antigens vary in their affinity and avidity. As such, their working dilutions range from 1:5,000 to about 1:32,000. However, one of ordinary skill in the art may readily determine the optimum dilutions for a given sample and assay by methods standard in the art such as checkerboard titrations.

Initially, all categories of patient samples were tested with the WR0130E *L. donovani* antigen (ATCC strain 30503). However, the assay was not sensitive to CL patient sera samples. Thus, these CL samples were retested with the *L. mexicana* (ATCC strain 50157) antigen.

The immunoassay of the present invention may detect IgM and IgG antibodies in human patients with visceral and cutaneous leishmaniasis, and dogs with canine leishmaniasis. When using *Leishmania*-specific IgG antibodies as a marker for active disease the test showed an overall sensitivity of 95.9% (261/272) and a specificity of 100%.

Water Homeostasis in the Human Body

Osmotic pressure is a force produced by the unequal distribution of diffusible ions across a biological membrane. Osmotic pressure can cause rapid water shifts leading to dehydration or cell lysis. Because body fluids are isosmotic, cells are not subjected to osmotic pressures in the human body. They are, however, subjected to other non-osmotic pressures, in vivo, such as hydrostatic pressure generated by cardiac function. Blood pressure forces water across semi-permeable membranes and this movement of water is counterbalanced in vivo by plasma colloid osmotic pressure. Colloid osmotic pressure (COP) or oncotic pressure is generated by the unequal distribution of osmotically active but non-diffusible molecules across biological membranes. In the human body, COP is generated by the unequal distribution of proteins in the respective body fluids. The COP of a molecule is inversely proportional to its molecular weight.

Because of its relative concentration and size, albumin is primarily responsible for the COP of body fluids. Albumin is synthesized and secreted by liver cells and its concentration in plasma is tightly controlled. Genetic (Nagase analbuminemia) or pathological conditions that lead to a decreased production (liver disease) or increased loss of albumin through the gastrointestinal (protein losing enteropathies) or urinary (nephrotic syndrome) system can lead to hypo-albuminemia. These conditions are frequently associated with either a derangement in free water distribution or a compensatory increase in globulin or lipid concentration to maintain physiologic COP. Additionally, when cells or tissues are constantly subjected to abnormally high blood pressures, they show pathology over time. The pathological changes include deposition of lipid in the wall of blood vessels.

Figure 10A:
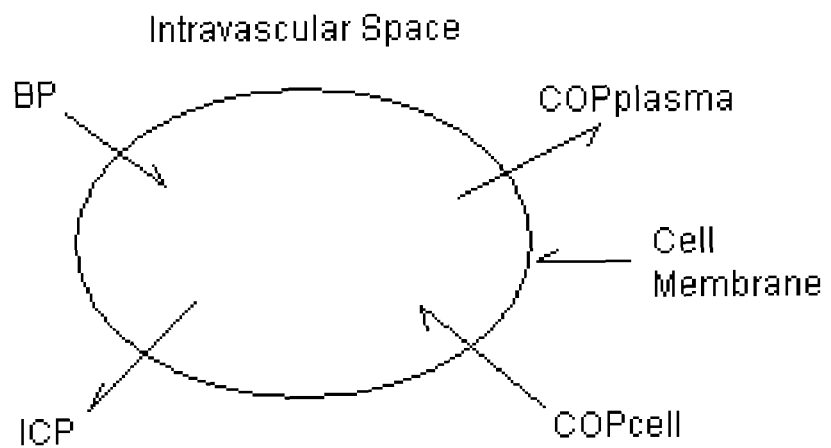
FIG. 10A is a schematic depicting forces affecting free water movement across membrane of a cell in the IVS.
Figure 10B:
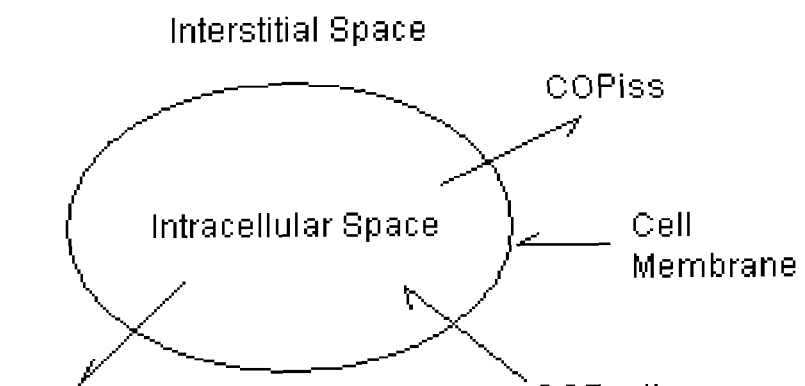
FIG. 10B is a schematic depicting forces affecting free water movement across membrane of cell in the ISS.

Water comprises over 90% of the human body by weight. Free water is distributed within three compartments—the intracellular space (the space within cells; ICS); the interstitial space (the space between cells; ISS) and the intravascular space (the bloodstream; IVS). The IVS is under positive blood pressure (BP) whereas the ISS is depressurized. The pressure in the ICS varies with cell type and the degree of hydration of the cell. The forces acting on the semi-permeable plasma membrane of a cell in the IVS and ISS are depicted in FIGS. 10A and 10B, respectively. In FIG. 10A, BP is counteracted primarily by COPplasma where:

COPplasma+ICP=BP+COPcell.

In the depressurized interstitial space depicted in FIG. 10B, the drop in pressure is associated with a concomitant drop in COPiss. Hence:

ICP=COPiss+COPcell.

Figure 11A:
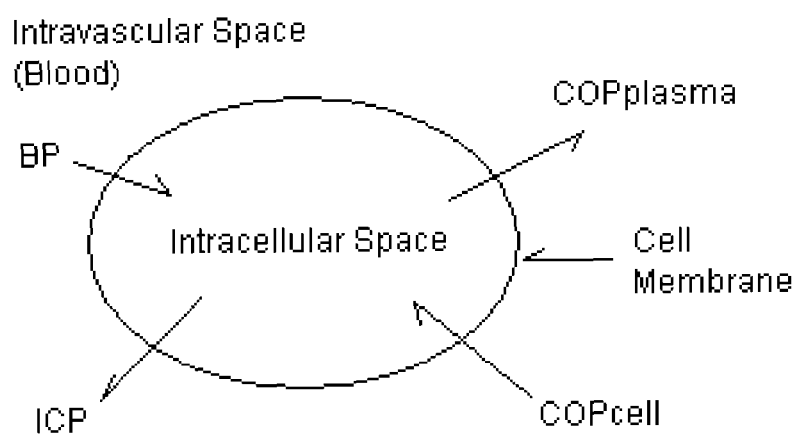
FIG. 11A shows that cells ex vivo can be maintained in plasma.
Figure 11B:
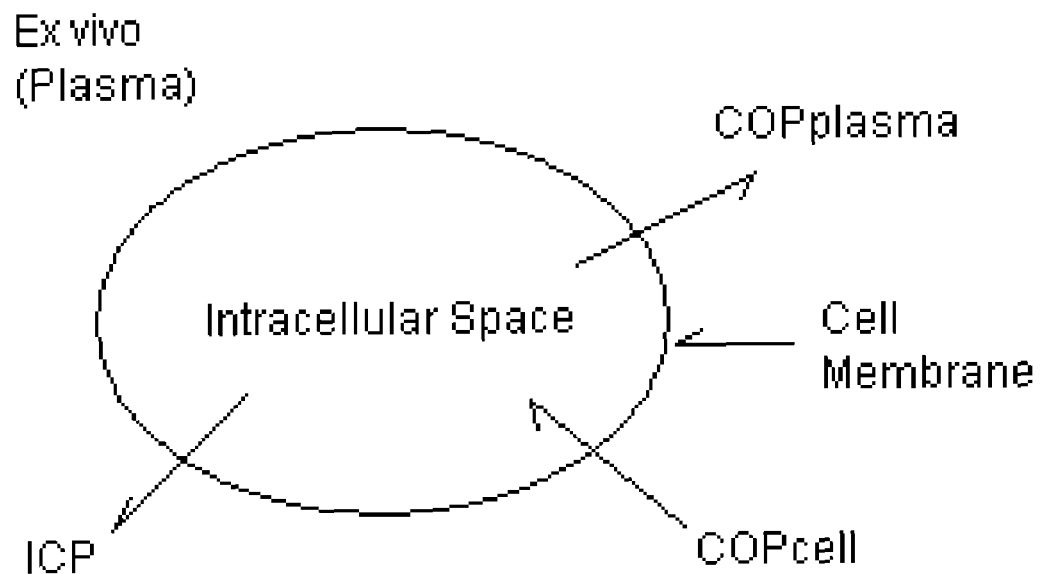
FIG. 11B shows that cells ex vivo can be maintained in nutrient media.
Figure 11C:
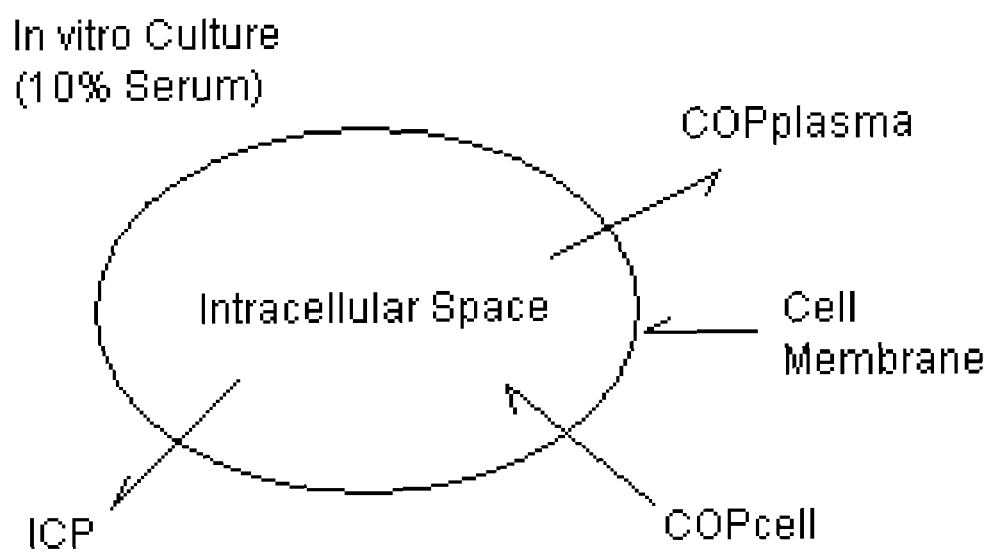
FIG. 11C shows that cells ex vivo can be maintained in nutrient media supplemented with 10% serum.

Ex vivo, cells can be maintained either in plasma (FIG. 11A), nutrient media (FIG. 11B) or nutrient media supplemented with 10% serum (FIG. 11C). In FIG. 11A, COPplasma acts on the cell membrane unopposed by BP and dehydrates the cell. In FIG. 11B, both BP and COPplasma are eliminated, but the vectorial force difference between ICP and COPcell causes a net movement of water that slowly leads to cellular dysfunction and death. When culture media is supplemented with 10% serum or the corresponding weight of colloid, water homeostasis is re-established in vitro and the cell thrives. See FIG. 11C. Under physiological conditions, the sum of the forces and net flow of water across the cell plasma membrane equal zero.

Normal cells like leukocytes traverse the IVS and enter into the ISS to contain an infection. Metastatic cells and pathogens also migrate between the two body compartments. FIG. 10A, depicts a cell or parasite in the pressurized IVS. In this environment, BP is counterbalanced predominantly by the COP of dissolved plasma proteins. In the ISS which is depressurized, FIG. 10B, albumin concentration is proportionally lowered to maintain water homeostasis. Despite the pressure difference between the two compartments, a cell migrating between the IVS and ISS thrives without expending significant energy reversing net water fluxes. This occurs because the loss in hydrostatic pressure in the ISS is associated with a concomitant drop in albumin concentration and COP. Plasma albumin concentrations outside the range of 40 gm/l to 50 gm/l are pathological. In conditions where albumin concentration falls below 20 gm/l, water is translocated into a third compartment and clinical ascites, edema or anarsaca results. Hyperalbuminemic states are rare. In Nagase analbuminemic rats (NAR), the absence of albumin is compensated by increased globulins and lipids resulting in normal plasma volume, interstitial fluid volume, and COP. NAR provides a rare example of water homeostasis in the complete absence of albumin.

Water Homeostasis Ex Vivo

Ex vivo, water homeostasis does not raise immediate concerns because cells are routinely cultivated in isosmotic media and the environment is depressurized. Tissues are also perfused or bathed in isosmotic media immediately after removal from the body. However, for long term propagation of cells, serum must be added to the base isotonic nutrient solutions. The optimal concentration range of serum in culture media is 10 to 20%. The rationale for adding serum to cell culture media is unclear and based on empirical evidence. A need for ill-defined serum factors and the detoxification properties of serum proteins, in particular albumin, is implied but remains unproven. Serum is a complex amalgamation of molecules that serve multiple functions. The various serum factors and the mechanisms by which they preserve cells and tissues in culture are presently unknown and are the object of this invention.

In addition to the re-establishment of water homeostasis ex vivo, cells depend on several other factors for growth and long term preservation. However, these factors are well known in the practice of the art and are routinely employed in cell culture and tissue preservation. Such factors include essential amino acids, salts, vitamins, nucleosides, water, glucose, trace metals and constant hydrogen ion concentration, gas tension, and temperature. Furthermore, specific cells may require specific additives from animal serum because of an inability to synthesize the requirement de novo. Addition of this requirement is consistent with the practice of this invention.

1. Cultivation of Human Parasites

Malaria is an important global infectious disease. It is estimated that 300 to 500 million new cases of malaria occur annually. Only four of several known species of the genus *Plasmodia* infect humans. The most malignant species is *P. falciparum*. *P. falciparum* is also the only species that can be propagated in culture. *Plasmodia* are obligate intra-erythrocytic parasites. Animal serum (10 to 20%) and erythrocytes must be added to growth media to sustain malaria parasites in culture.

The primary role of serum in parasite growth media, such as those used for cultivating *P. falciparum*, is to provide albumin and the appropriate COP required to maintain water homeostasis. *P. falciparum* parasites were cultured in plasma, ex vivo and in culture medium supplemented with 10% serum. Parallel *P. falciparum* cultures were set with serum replaced by increasing concentrations of bovine albumin. Parasites in medium supplemented with 10% serum served as controls. Media were changed daily and the parasitemia on day 5 determined by Giemsa-stained smears. The growth at any given albumin concentration was calculated relative to parasitemia in control serum-supplemented cultures. The relative growth rates were plotted (y-axis) against albumin concentration (x-axis). The experiment was repeated 8 times.

It was found that the parasites thrive in a medium supplemented with 10% fetal bovine serum. In contrast, parasites fail to thrive in undiluted plasma because in a depressurized culture environment COPplasma moves water out of the cell unopposed by BP. In experiments where varying concentrations of bovine albumin was used in place of serum, optimal growth of malaria parasites was observed at albumin concentrations of about 4 to about 5 gm/l.

The normal concentration of albumin in plasma is about 40 to about 50 gm/l and 10% plasma normally contains about 4 to about 5 gm/l albumin. Hence, the observed albumin concentration needed for growth of *P. falciparum* parasites in the bovine albumin experiments herein is about 10% plasma, i.e. about 4 to about 5 gm/l albumin.

Other pathogenic parasites, including *Leishmania* and Trypanosomes, can be cultivated in vitro. Table 1 and Table 2 show *Leishmania* and Trypanosomes growth rates when propagated in a medium (BAM) where 5 gm/l bovine albumin was used in place of 10% serum.

TABLE 1

Comparison of Growth Rates of Four Strains of *P. falciparum* in Serum-supplemented and Serum-free

| P. falciparum Strains | Routine Serum-supplemented Medium | Serum-free Medium (BAM) |
|---|---|---|
| W-2 (S.E. Asia) | 32.4% | 31.8% |
| FCV (Vietnam) | 67.4% | 44.6% |
| NF-54 (Holland) | 17.6% | 20.6% |
| ITG2F6 | 24.4% | 15.4% |

TABLE 2

Growth Rates of Parasites in Serum- and Albumin-supplemented (BAM) Media

| Parasite | Day 0 | Day 3 Serum | Day 3 Albumin (BAM) |
|---|---|---|---|
| *L. donovani* (Sudan) NLB-064E | $1.3 \times 10^6$ | $1.1 \times 10^7$ | $6.2 \times 10^6$ |
| *L. donovani* (India) NLB-328 | $1.0 \times 10^6$ | $1.9 \times 10^7$ | $3.6 \times 10^6$ |
| *L. mexicana* NLB-357 | $1.0 \times 10^6$ | $4.6 \times 10^7$ | $3.6 \times 10^6$ |
| *L. major* (Kenya) NLB-1149 | $3.7 \times 10^6$ | $1.8 \times 10^7$ | $4.3 \times 10^6$ |
| *Herpetomonas* spp. NLB-335A | $7.0 \times 10^6$ | $3.8 \times 10^7$ | $8.1 \times 10^6$ |

As provided herein, the present invention provides methods and media for cultivating cells in vitro using media containing an oncotic agent which media is free of proteins, including animal-derived proteins. Table 3, shows the growth rates of *Leishmania* parasites in media where xylose, sorbitol, sucrose, or ficoll were used as the oncotic agent in lieu of bovine albumin. Despite the fact that parasite viability was not significantly different between the oncotic agents, xylose and sorbitol are preferred because they are plant-derived, inert and have low molecular weights. As provided herein, a xylose-supplemented medium (XOM) was used for the experiments herein.

TABLE 3

Viability of *L. tropica* Promastigotes in Media Supplemented with Various Colloids

| | Bovine Albumin (BAM) | Sucrose (SUM) | Ficoll (FIM) | Sorbitol (SOM) | Xylose (XOM) |
|---|---|---|---|---|---|
| Day 0 | | | | | |
| Motility | 3+ | 2+ | 3+ | 3+ | 3+ |
| Rosette | 2+ | 2+ | 2+ | 2+ | 2+ |
| Day 1 | | | | | |
| Motility | 3+ | 2+ | 3+ | 3+ | 3+ |
| Rosette | 2+ | 2+ | 3+ | 3+ | 3+ |
| Day 4 | | | | | |
| Motility | 4+ | 3+ | 3+ | 4+ | 4+ |
| Rosette | 4+ | 3+ | 3+ | 4+ | 4+ |

The protein-free medium of the present invention may be used to obtain molecules secreted by cells being cultivated. The molecules include potential immunodiagnostic and prognostic markers for various phenotypes and biological functions. The secreted molecules can bind and be modified by proteins commonly found in prior art media. Thus, the present invention provides a method for obtaining functional molecules secreted by cells which are unadulterated by proteins found in prior art culture media. The present invention provides a simple technique for the procurement of molecules secreted by cultivated cells that is uncontaminated by extraneous animal proteins and need not be purified or isolated from culture media proteins.

Purification is tedious, expensive and decreases yield. More importantly, trace amounts of animal protein contaminants can render these products unsuitable for in vivo use. The molecules secreted by cells cultivated in protein-free media may be used as immunodiagnostic markers or as vaccine products, e.g. soluble antigens obtained from cultivating *Leishmania* parasites in protein-free culture medium as provided herein.

Three pairs of growth media were prepared for the propagation of *Leishmania* parasites. The first medium was supplemented with 10% fetal calf serum (FCS). The other two media were supplemented with 5 mg/ml bovine albumin (BAM) and 0.011 mg/ml xylose (XOM), respectively. Hence, BAM is a serum-free and XOM a protein-free medium. *L. donovani* promastigotes were cultivated in each of the three media at 26° C. for 5 days with no medium changes. At the end of the experiment the medium-pairs (with and without parasite) were run by polyacrylamide gel electrophoresis (SDS-PAGE) and silver-stained to show the proteins released by the parasite. Fresh media were used as controls. The parasite proteins were unequivocally observed in the XOM medium only. In the other two media, animal protein in the medium obscure parasite products. XOM was then utilized to demonstrate the proteins released by various *Leishmania* Old World strains.

To show proteins secreted into protein-free medium (XOM) by various Old World *Leishmania* species, *L. donovani, L. amazonesis, L. major*, and *L. tarentole* promastigotes were seeded into XOM at $1 \times 10^6$/ml and incubated at 26° C. The media were harvested on day 5 and protein separated by SDS-PAGE. The gel was silver-stained to show protein bands. The SDS-PAGE showed proteins released by *Leishmania* promastigotes into spent protein-free medium and the control medium that received no parasites showed no protein bands.

Figure 12:
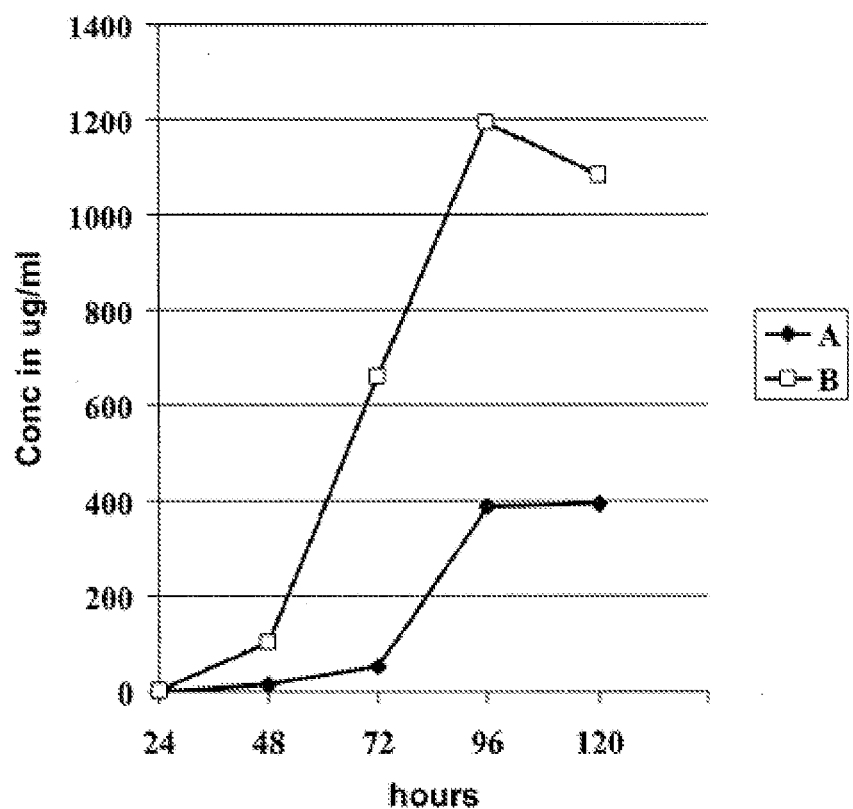
FIG. 12 shows secretion of protein into protein-free Medium (XOM) by *L. donovani* promastigotes.

In another experiment, *Leishmania* parasites were seeded into XOM at $1 \times 10^7$/ml or $1 \times 10^6$/ml and the rate of accumulation of parasite proteins in the medium measured. Medium was taken at timed points and centrifuged at 9000×g for 30 minutes. The protein concentration of the supernatant was measured by UV (280) spectroscopy. Antigen concentration in μg/ml (y-axis) was plotted against time in hours (x-axis). Protein accumulation peaked after about 72 hours as shown in FIG. 12. A peak level will not have been observed if the proteins resulted from the disintegration of non-viable parasites.

Further evidence that protein procured in this manner were of biological significance was obtained from experiments using patient sera. Patients make specific antibody when exposed to foreign antigens. Therefore, the serum of subjects having leishmaniasis should contain antibodies to parasite products to which the subject is exposed during the parasite infection.

In an experiment to test the clinical utility of protein free medium such as XOM, the protein content of the *Leishmania* parasite-conditioned medium was separated by SDS-PAGE and transferred unto nitrocellulose paper and blotted with sera from subjects with leishmaniasis and controls. Specifically, soluble antigen prepared as described herein was probed with polyclonal antibody, sera from Kala azar patients and controls: anti-*Leishmania* polyclonal antibody unconjugated and anti-rabbit-IgG-HRP (positive control), anti-*Leishmania* polyclonal antibody-HRP (positive control), SKM (negative control), LYI (negative control), and sera from two subjects clinically diagnosed with visceral leishmaniasis.

Soluble antigen obtained from XOM specifically bound with antibodies in the sera of the subjects suffering from leishmaniasis. Thus, soluble antigens released into protein free medium such as XOM have functionally similar immunological activity as native antigens released into the patients and may therefore be used as assay reagents due their substantially similar biological properties and binding affinities and specificities. Therefore, proteins secreted in protein-free media, such as XOM, may be utilized in assays such as immunoassays. In fact, soluble antigens according to the present invention were successfully employed to show a decrease in antibody titers in a subject suffering from visceral leishmaniasis six months after anti-leishmanial chemotherapy. Therefore, the present invention provides methods and reagents for monitoring treatments.

A. Vaccines

The vaccine potential of antigens procured in XOM is exemplified by experiments with BALB/c mice provided herein. In contrast to C3H mice which are resistant, BALB/c mice invariably succumb to infection with *L. major*. Rodent susceptibility to leishmaniasis has been shown to relate to the T cell response mounted by the mouse to the parasite infection. C3H mice mount a Th1 type response and are resistant whereas susceptible BALB/c mice are Th2 responders. T cell production of interferon gamma (IFN-g) upon stimulation with antigen is indicative of a Th1 type response. IL-4 production is similarly linked to a Th2 response.

Exo-antigen from *L. major* parasites (Lms/e) was procured in XOM as provided herein. BALB/c mice were divided into two groups. The mice in one group were each given a single subcutaneous injection of Lms/e (50 μg) without adjuvant. Ten days later, the mice in both groups were challenged with 100,000 *L. major* parasites subcutaneously in the hind footpad. Vaccinated mice showed protection (lesion size, monitored at 7, 14 and 21 days, smaller at all time points; $p<0.05$, t-test analysis). T cells were then obtained from infected mice and stimulated in culture with either parasite lysate antigen or Lms/e. Lms/e induced a Th1 response as shown in Table 4.

TABLE 4

Cytokine Production by Lvmphocvtes from *L. major* Infected BALB/c Mice Stimulated in Culture with Promastigote Lvsate versus Antigen Secreted into Protein-free Medium, XOM

| Antigen | IFN-g (ng/ml) 24 hrs | IFN-g (ng/ml) 48 hrs | IL-4 (pg/ml) 24 hrs | IL-4 (pg/ml) 48 hrs |
|---|---|---|---|---|
| None | 0.1 | 0.4 | 7.7 | 29.6 |
| Parasite Lysate (5 μg/ml) | 0.3 | 0.1 | 134.5 | 491.0 |
| Lms/e (10 μg/ml) | 1.0 | 2.7 | 5.9 | 5.8 |

Therefore, the protein free medium according to the present invention may be used to procure antigens for use as immuno-regulatory agents to include vaccines.

B. Hvbridoma Cell Lines

Monoclonal antibodies (MAbs) are valuable tools for research because of their unique specificity. They can make an even greater impact in clinical diagnosis and treatment. Despite the fact that hybridomas have already been constructed to several thousand specificities, their impact on clinical practice is limited by the non-availability of pure and affordable product. The commonly used techniques for MAb production utilize animals or animal-derived products. Hence, the downstream separation of MAb from animal protein contaminants is cumbersome, costly and low yield. More importantly, MAbs extracted from animal ascites fluids or serum supplemented production systems are unsuited for in vivo use, because trace amounts of foreign protein can cause fatal adverse reactions.

The present invention provides a method of producing MAbs which comprises cultivating a hybridoma of any specificity in the protein free medium of the present invention. Such MAbs are not contaminated with animal protein and are suitable for in vivo and clinical use.

Five hybridoma cell lines were separately seeded into XOM at $1\times10^7$ per ml and the rate of accumulation of protein in the media monitored at UV 280. Protein concentration was calculated from a standard albumin curve. Protein concentration y-axis, μg/ml, was plotted against time (x-axis, days). All of the cell lines secreted protein with peak values ranging from about 0.6 to about 1.9 mg/ml. It should be noted that MAb concentrations achievable in mouse ascites fluid are in the mg/ml range. Therefore, the present invention provides methods for obtaining MAbs free of protein contaminants.

The various hybridoma-conditioned media were serially diluted on 96 well microtiter plates. The wells were blocked with albumin and incubated with goat anti-mouse IgM (whole molecule) conjugated with HRP. Wells were then washed and substrate (ABST) added. Optical density (y-axis) was plotted against antibody concentration.

The procured proteins were shown to be functional antibody by ELISA and Western blot techniques. In the ELISA experiments 10 μg/ml protein from each hybridoma-conditioned medium was serially diluted in a 96-well microtiter plate and the wells blocked. A commercially available tagged anti-mouse antibody which specifically binds to the Fc portion of an IgM antibody or IgG antibody was used to determine the immunoglobulin class of the MAb secreted by the various cell lines. Only one hybridoma secreted IgM and all five secreted IgG.

In the Western blot experiments, the proteins in the hybridoma-conditioned media were separated by SDS-PAGE in duplicate and transferred unto nitrocellulose paper. One set of transferred proteins was probed with goat anti-mouse IgM (u chain) and the other with goat anti-mouse IgG (whole molecule). IgM specific bands were seen only with hybridoma identified as secreting IgM by ELISA, whereas the IgG specific bands were noted with all hybridoma cell lines. Therefore, the Western blot data corroborate the ELISA results in the identification of the class of immunoglobulin secreted by the hybridoma cells into the XOM-medium.

Proteins secreted into XOM by the hybridomas were separated by SDS-PAGE, transferred unto nitrocellulose and probed with anti-mouse chaperone antibodies: PDI; ERP72; ERP61; GR94; ERP60 (all kindly donated by Dr. Michael Green of St. Louis University, St Louis, Mo.) and anti-mouse IgG. Specifically, XOM was seeded with $1\times10^6$/ml bybridoma cells and secreted proteins were separated by SDS-PAGE and transferred onto nitrocellulose paper. The paper was blocked with blotto and cut into stripes. The stripes were separately probed. A secondary antibody tagged with a reporter system was used to show reaction with the probe. Mouse IgG positive bands indicate position of immunoglobulin chains. A band positive with both an anti-chaperone and anti-IgG antibody indicates linkage of antibody to its chaperone protein. Western blots showed dissociated chaperone proteins PDI and ERP 72 in XOM. The Western blots also showed that the respective chaperone proteins co-locate with IgG. These results indicate that intact antibody molecules, their component chains and associated chaperone proteins are accessible in pure form in conditioned protein-free media.

The use of protein-free medium, such as XOM, in the procurement of component immunoglobulin chains is further illustrated in an experiment where hybridoma-conditioned XOM was subjected to various denaturing conditions and then separated on SDS-PAGE. The resulting immunoglobulin components were transferred to nitrocellulose paper and probed with anti-mouse IgG whole molecule. Addition of SDS and glycerol resulted in two IgG immunoglobulin species. The heavier species had a MW of 98 Kda. Addition of 3-mercaptoethanol (3-ME) reduced the size of this heavier species from MW 98 Kda to about MW 50 Kda. Boiling the sample in the presence of 3-ME, however, led to the disintegration of the heavier species. These experiments indicate that XOM can be utilized to procure both the intact functional antibodies plus the component chains and chaperone proteins. Thus, the present invention allows the ability to procure specific antigen/Fab complexes without linkage to in vivo effector systems.

C. Normal Human Cells

Human cells release substances into the bloodstream that modulate local and systemic function. For example, Beta-islet cells in the pancreas secrete insulin in response to a glucose load. Insulin facilitates cellular uptake and catabolism of glucose to generate cellular energy. The list of mediators of cellular function is known in the art and includes cytokines, hormones, ecosanoids. The cells that synthesize and release these mediators into the bloodstream have been identified and some can be maintained in tissue culture. Pathological conditions exist where clinical administration of a mediator can lead to complete resolution of the disease. For example, the inability to secrete insulin after a glucose load engenders a chronic debilitating and potentially fatal disease, diabetes mellitus. The signs and symptoms of diabetes can be reversed by the administration of exogenous insulin. Insulin used in clinical practice to treat diabetes mellitus is extracted from the pancreas of domestic animals like cows and pigs. More recently, recombinant insulin has been introduced into the market for the management of diabetes but this is a recombinant rather than a natural product. Recombinant proteins are synthesized by bacteria, fungal or baculovirus systems.

Normal human cells like pancreatic islet cells are not routinely cultivated in vitro, thus, human proteins, such as human insulin, are not commercially available at affordable prices. Thus, the present invention provides methods and culture media for obtaining pure human cellular products including cytokines, hormones, ecosanoids, and growth factors. As exemplified herein, normal human lymphocytes and monocyte-derived macrophages were cultivated in protein-free media according to the present invention. Monocyte-derived macrophages from a healthy volunteer were harvested off a Ficoll gradient, washed and a mono-layer established on 24 well plates. The monolayer was overlaid with XOM and the accumulation of protein in the medium monitored by UV spectroscopy for 10 days. A peak protein level of about 351 μg/ml at 192 hours was observed.

In another experiment, monocytes were harvested from venous blood of two subjects and plated on 24 well culture plates. The adherent macrophage layer was washed several times with XOM and overlaid with fresh XOM. Conditioned medium from designated wells was aspirated at stated times and pooled. The proteins in spent media were separated on a SDS-PAGE preparatory gel designed to elute specific proteins (Bio-Rad, Hercules, Calif.). The comb generated two wells along each lateral border of the gel and a horizontal trough between the wells. Molecular weight markers were run in the two lateral wells and the macrophage proteins were placed in the trough. After separation, the two lateral edges of the gel were cut, to include the MW standards and edges of the separated proteins and silver-stained. These gel slices (two slices per gel) served as a template for excision of the section of the gel containing the desired protein band. The protein banding patterns from the two subjects look strikingly similar. The portion of unstained gel containing the most prominent protein band was cut and the protein eluted.

In another experiment, lymphocytes from a healthy subject were harvested off a Ficoll gradient, washed and stored at either 4° C. or 25° C. in BAM ($1\times10^6$/ml) for 7 days. At timed intervals, the lymphocytes from a temperature-set of tubes were harvested, washed and transferred into XOM at 37° C. The amount of protein in the medium was measured after 4 and 8 days in XOM. The results in Table 5 show that lymphocytes stored at 4° C. subsequently release more protein in XOM than those stored at 25° C. The amount of protein released did not change significantly between 4 and 8 days incubation in XOM. This observation argues against cell death as the mechanism of protein release into the medium as significantly more protein would have been expected from the 8 day harvests.

TABLE 5

Protein accumulation in XOM from lymphocytes stored for various time periods in BAM

| Storage in BAM (hrs) | Storage Temp | Culture in XOM 4 days (mg/ml) | Culture in XOM 8 days (mg/ml) |
|---|---|---|---|
| 0 | 4° C. | 0.6 | 1.0 |
| 24 | 4° C. | 1.3 | 1.5 |
| 24 | 25° C. | 1.2 | 1.4 |
| 48 | 4° C. | 2.0 | 3.5 |
| 48 | 25° C. | 1.5 | 1.5 |
| 72 | 4° C. | 1.3 | 1.9 |
| 72 | 25° C. | 0.4 | 0.4 |
| 96 | 4° C. | 2.5 | 2.6 |
| 96 | 25° C. | 1.0 | 0.7 |
| 168 | 4° C. | 0.8 | 1.0 |
| 168 | 25° C. | 0.7 | 1.0 |

Lymphocytes were harvested from three healthy subjects, washed and seeded into XOM. A lymphocyte-derived cell line (MG-63, ATCC) which served as a control was also seeded into XOM. MG-63 is an osteosarcoma cell line that secretes IL-6 after stimulation with human IL-1B. The secreted proteins were separated on SDS-PAGE transferred unto nitrocellulose paper and then stained with Amido Black. The human lymphocytes showed several common bands between the subjects whereas no bands were present in the control medium (XOM) and medium conditioned by MG-63. Monocyte-derived macrophages from two subjects were seeded into XOM and the secreted proteins separated by SDS-PAGE and visualized after silver staining The protein profiles of macrophages from the two subjects were similar but unlike that from cultivated human lymphocytes. A subject whose macrophage proteins had been collected and stored, subsequently became infected with P. falciparum parasites. Macrophage proteins were collected from monocytes harvested during the malaria infection. SDS-PAGE and Western blot showed similar protein profiles between the two harvests.

In another experiment, macrophage-conditioned-XOM was prepared as described and the released proteins separated by SDS-PAGE. The most prominent band noted was cut and eluted from the gel. The eluted protein was found to migrate as a single band with an identical molecular weight (MW 55.6 KDa) as the most prominent protein produced by lymphocytes. The identity of the eluted protein was established by separately probing stripes of nitrocellulose paper with antibodies to the following human cytokines: Interferon gamma (IFN-g), IL-2, IL-3 and IL-6. Positive bands were observed only on the stripe probed with anti-human IL-6, which is a multifunctional protein associated with acute phase reactions and produced by activated lymphocytes and monocytes (macrophages), fibroblasts and endothelial cells. The eluted IL-6 was lyophilized and shown to be stable after lyophilization.

Milligram amounts of this cytokine as well as others known in the art can be readily procured using the protein-free medium and methods of the present invention in combination with methods known in the art. IL-6 produced using the methods of the present invention was run on SDS-PAGE with a commercially available recombinant human IL-6 and secreted proteins from human lymphocytes. In contrast to the recombinant product, which show multiple protein bands, the IL-6 from XOM ran as a single band, an indication of 100% purity. Thus, protein-free medium (XOM) can be used to procure pure human IL-6 from normal human lymphocytes and macrophages. Table 6, shows a comparison of commercially available IL-6 products (Sigma Chemical Company, St. Louis, Mo.) to 1 mg protein produced using the protein-free medium of the present invention (WRAIR IL-6). Sigma Chemical Company carried three human IL-6 products in its 1999 catalogue. Two of these items are recombinant proteins (I 7764 and I 1395) and one natural (I 3268).

TABLE 6

Comparison of WRAIR IL-6 to Commercially Available Products

| Catalogue # | Origin | Purity |
| --- | --- | --- |
| I 7764 (Recombinant IL-6) | E. coli | >98% pure by SDS-PAGE |
| I 1395 (Recombinant IL-6) | E. coli | >97% pure by SDS-PAGE |
| I 3268 (Natural IL-6) | MG-63 osteosarcoma cells + Human IL-1B | >90% pure by SDS-PAGE |
| WRAIR IL-6 (Natural IL-6) | Human macrophages in XOM | 100% pure by SDS-PAGE |

Table 6, also shows the value purity adds to these biological products. The difference in purity between the two recombinant products (greater than about 97% versus greater than about 98%). WRAIR IL-6 on the other hand is 100% pure as evidenced by SDS-PAGE.

Therefore, the present invention provides methods for obtaining pure cellular products, including human insulin. As provided herein, cells can be cultivated in protein-free medium and cellular products of interest may be separated from the conditioned medium using methods known in the art. Cell products can be concentrated or lyophilized for long-term storage using methods known in the art.

D. Preservation of Cells or Tissues

Advances in medical technology have increased the demand for healthy tissue. This demand will increase in the future as affluent populations age and need replacement organs. The availability of animal tissue is presently limited by our inability to preserve cells and tissues. Cells and tissue have to be transplanted soon after removal because of the lack of knowledge on how to preserve them. Another impediment to the more widespread use of replacement organs is immune rejection from tissue incompatibility. Pains taking procedures are needed to match donor tissue to recipient. This problem can be partly circumvented by banking tissue for future autologous transplantation.

Yet another demand for human cells and tissue is for stem cells. Stem cells harvested from embryonic and/or adults tissue are believed to hold promise for use in the treatment of debilitating and life-threatening diseases and the regeneration of new tissue that are lost through accident, aging and disease. Dramatic rise in the demand for stem cells in research and medical treatment are expected after the ongoing ethical and philosophical debates are resolved.

Cryopreservation is the present method of choice. A major drawback to cryopreservation, however, is the expenses to keep the needed tissue or cells at the required temperatures. Additionally, the factors that induce cellular breakdown immediately after cells and tissues are removed from the body are presently unknown. Elucidation of these processes can lead to the development of appropriate counter measures. Perfusion fluids that have been formulated for tissue preservation contain essential salts and nutrients. They are buffered and isotonic but do not contain animal proteins. Added animal proteins can cause post-transplantation adverse reactions. As is the case with cell culture media, COP is ignored in the design of perfusion fluids.

This invention claims that the failure of cells and tissues to thrive ex vivo is related to COP and net water fluxes across cell membranes. Adaptations that ensure survival in their native environments become lethal ex vivo because of the absence of hydrostatic pressure. Experiments to illustrate embodiments of this claim were not performed because of the need for organ perfusion systems. Nonetheless, this principle was used to preserve and transport malaria parasites from the field to a centralized laboratory. Malaria parasites fail to thrive after removal from the patient. They can be preserved either by cryopreservation in liquid nitrogen or storage at −70° C. These techniques used for long term storage are too labor-intensive and expensive for routine use. With the advent of parasite resistance to multiple drugs, the drug sensitivity profile of the parasite is required for the timely administration of effective chemotherapy. Hence, simple techniques are needed to hold parasites between venipuncture and laboratory drug sensitivity determination. Transit time can vary between a few hours to less than a week. Because of the clinical demand for such a service, BAM was evaluated in the field as a transport medium for malaria parasites.

Although, BAM used in these experiments is not protein-free, the principle behind formulating BAM and XOM is the same—balance oncotic pressures in the medium using colloid. However, in BAM, bovine albumin is the colloid, whereas xylose is the colloid in XOM. XOM becomes the medium of choice when contamination from animal protein is an issue as it is in perfusion fluids. In transport medium this is not the case and BAM was used. Incidentally, XOM is a more restrictive medium than BAM as it excludes all animal proteins to include those whose functions are not essential but needed for optimal growth. Hence XOM is preferred over BAM in cases where animal protein must be excluded.

Table 7 shows that malaria parasites preserved in BAM during transit from the patient to the laboratory remained viable enough to permit determination of their drug susceptibility profile.

TABLE 7

Fifty percent inhibitory concentrations (IC50) of *P. falciparum* isolates against quinine, amodiaquine and chloroquine by the 48 hour parasite lactate dehydrogenase (48 hr pLDH) assay after transport from the field on ice. IC50 in nmol/Liter

| Isolate | % Parasit | Days in Transit | Amodiaquine | Chloroquine | Quinine |
|---|---|---|---|---|---|
| D86 | 7.3 | 1 | 29.8 | 33.2 | 175 |
| KilH | 8.4 | 1 | 124.6 | 248 | 378 |
| KilS | 6.0 | 1 | 128.2 | 122.4 | 186.8 |
| C108 | 4.4 | 2 | 86.2 | 256 | 159.8 |
| B106 | 5.6 | 2 | 99.2 | 294 | F |
| F166 | 2.5 | 1 | 91.6 | 29.8 | 93.2 |
| D166 | 3.1 | 2 | 6.6 | F | 79.8 |
| C166 | 1.3 | 1 | 68 | 30.8 | 164.6 |
| B116 | 1.1 | 2 | 145.4 | 35.2 | 136 |
| A116 | 1.9 | 1 | 70.2 | 58.4 | 152 |
| A246 | 3.5 | 1 | 17 | 20 | 16.3 |
| G296 | 3.8 | 2 | 179.2 | 400 | 306 |
| F296 | 1.2 | 1 | 202 | 66.4 | 99.2 |
| D296 | 2.2 | 1 | 180 | 166 | 999.2 |
| B296 | 4.8 | 2 | 53.4 | 664 | 1.8 |
| A296 | 5.0 | 1 | 151.6 | 114.6 | 476 |
| G17 | 2.9 | 1 | 40.8 | 52 | 143.4 |
| 1236 | 0.2 | 1 | 26.8 | 22.2 | 0.04 |
| H236 | 0.5 | 2 | 8.6 | 91.4 | 208 |
| G236 | 1.0 | 1 | 33.8 | 330 | 304 |
| B236 | 1.5 | 1 | 28.8 | 90.6 | 183.2 |
| E67 | 1.5 | 1 | 31.6 | 50 | 108 |
| C67 | 4.1 | 1 | 117.2 | 142.6 | 136 |
| A67 | 0.2 | 1 | 37.6 | 191.4 | <80 |
| F107 | 0.7 | 1 | 23.6 | 818 | F |
| E107 | 5.7 | 1 | 152. | 554 | 230 |
| D107 | 3.0 | 1 | 177.6 | 502 | 264 |
| A107 | 1.2 | 1 | 91.8 | 818 | F |
| C107 | 3.0 | 1 | 179.4 | 554 | 96.4 |
| L107 | 1.6 | 1 | 18.4 | 224 | 58.8 |
| K107 | 1.0 | 1 | 35.4 | 300 | 354 |
| J107 | 1.4 | 1 | 12.6 | 294 | 55.4 |
| 1107 | 1.3 | 1 | 6.6 | 160 | 40 |
| H107 | 12.4 | 1 | 100.2 | 180.4 | 28 |
| R107 | 4.2 | 2 | 79.8 | 78.8 | 472 |
| L137 | 3.3 | 1 | 149.6 | 320 | 134.2 |

IC50 are in nanomoles per liter test culture;
F = test failed;
ND = test not done.

In another trial, malaria parasites isolated from patients in a remote location were preserved in BAM for periods varying from a few hours to eight days. Survival rates between 80 and 100% were observed as shown in Table 8.

TABLE 8

Survival rate of *P. falciparum* isolates transported from the field to a central research laboratory in iced transport medium

| Number of days in transport medium | Survival Rate (%) |
|---|---|
| <1 (n = 2) | 100 |
| 1 (n = 35) | 91.4 |
| 2 (n = 24) | 83.3 |
| 3 (n = 13) | 84.6 |
| 8 (n = 5) | 80.0 |

Total (n = 79)
Survival rate (%) is the fraction of isolates that yielded positive cultures when cultivated in complete serum containing medium in the laboratory at CCR-KEMRI, after storage in iced transport medium. (13 cultures were contaminated. Contamination was linked to technician error at CCR-KEMRI).

Therefore, the present invention provides methods for preserving cells to include stem cells and tissues.

E. Barophylic Organisms

Despite the fact that barometric pressures reach extremely high levels on the ocean floor, hyperthermic vents are teeming with life. Microbes and giant tubeworms thrive in this apparently hostile environment because they have evolved mechanisms to withstand the high barometric pressures. When these organisms are transported to sea level, these same adaptive mechanisms become lethal and they fail to thrive. Unwieldy and expensive contraptions have been engineered at sea level to withstand the high hydrostatic pressures needed to ensure survival of these organisms away from their native environment. However, simulation of the required pressures limits access to the organisms of interest. The dilemma of applying high hydrostatic pressure while granting direct human access to the organisms is the subject of this claim of the invention.

Hence, barophylic organisms can be cultivated in open terrestrial systems where sufficient oncotic agent is added to the medium to simulate the hydrostatic pressures in their native environments. The amount of oncotic agent sufficient to cultivate a given barophylic organism may be readily determined using methods known in the art.

F. Insulin Production

Figure 13:
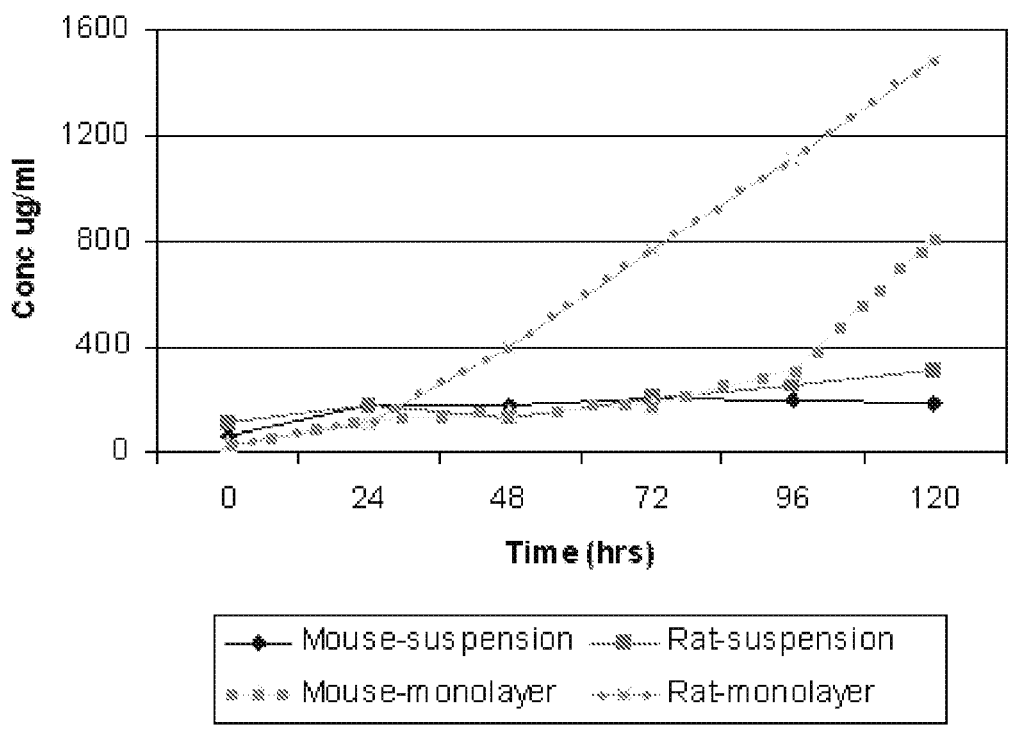
FIG. 13 shows the rate of secretion of protein by rodent beta-islet cells cultivated in protein-free medium supplemented with glucose (GFXOM). Mouse and rat beta-islet cells were cultivated in vitro in a protein-free medium (XOM) supplemented with D-glucose (GFXOM). Aliquots of supernatant were obtained at timed intervals and protein concentration measured by UV spectrophotometry.

Beta-islet cell line from a rat (ATCC CRL-2058 RIN-5F Lot #985637) and mouse (ATCC CRL-2055 NIT-1 Lot #1346069) were purchased from ATCC, Rockville, Md. They were cultured in XOM fortified with additional D-glucose (GFXOM). In both the rat and mouse cultures some cells adhered to the culture flask whereas others remained in suspension. Protein concentration was monitored separately in adhered and suspended cells. More protein was measured in the flasks with adhered cells particularly in the rat cell cultures where a total of about 1.5 mg/ml protein was produced after 120 hours of in vitro culture. See FIG. 13.

Figure 14A:
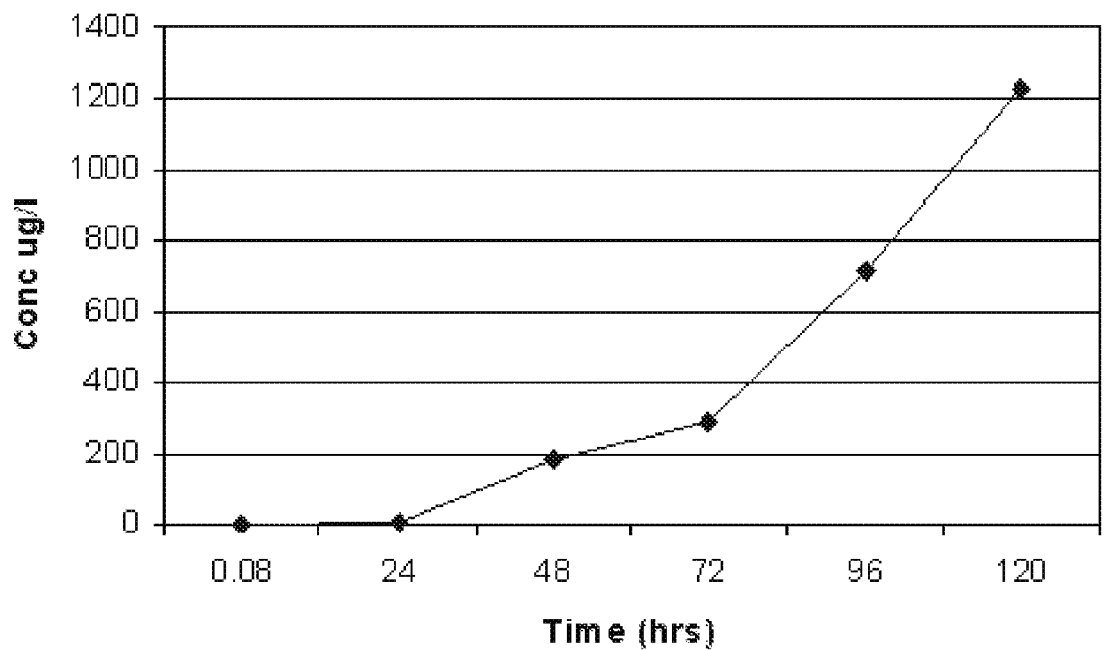
FIG. 14A shows insulin concentration in supernatant of mouse beta-islet cells cultivated in a protein-free medium (XOM) supplemented with D-glucose (GFXOM). Mouse beta-islet cells were cultivated as adherent cells in a protein-free medium (XOM) fortified with D-glucose (GFXOM). Insulin concentration in supernatant was determined by ELISA after 120 hours in culture.
Figure 14B:
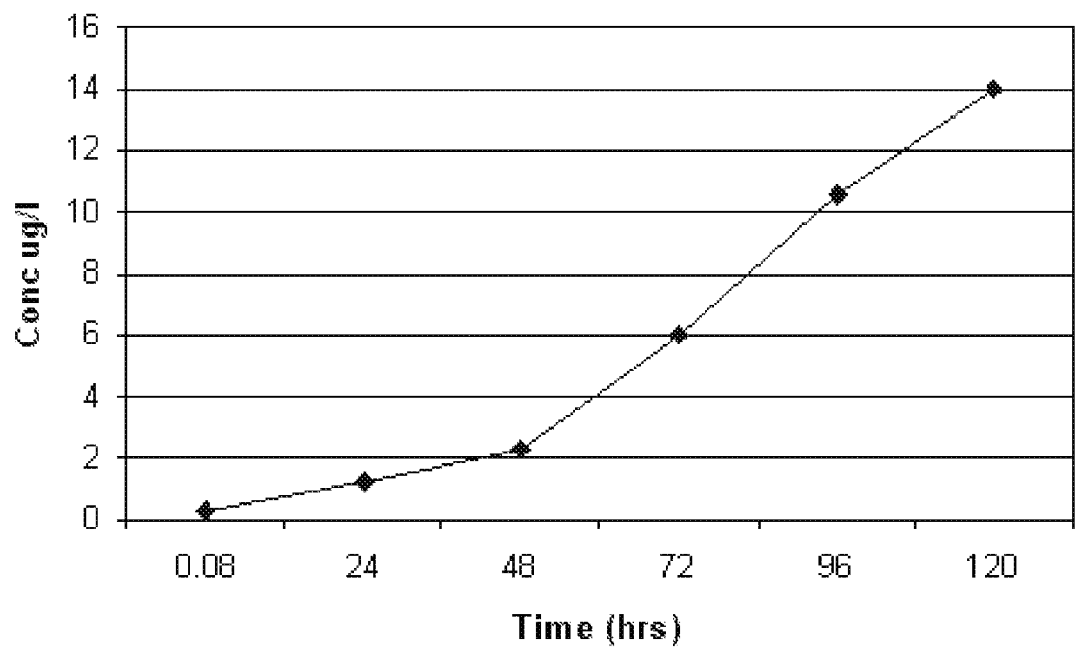
FIG. 14B shows insulin concentration in supernatant of rat beta-islet cells cultivated in a protein-free medium (XOM) supplemented with D-glucose (GFXOM). Rat beta-islet cells were cultivated as adherent cells in a protein-free medium (XOM) fortified with D-glucose (GFXOM). Insulin concentration in supernatant was determined by ELISA after 120 hours in culture.
Figure 15A:
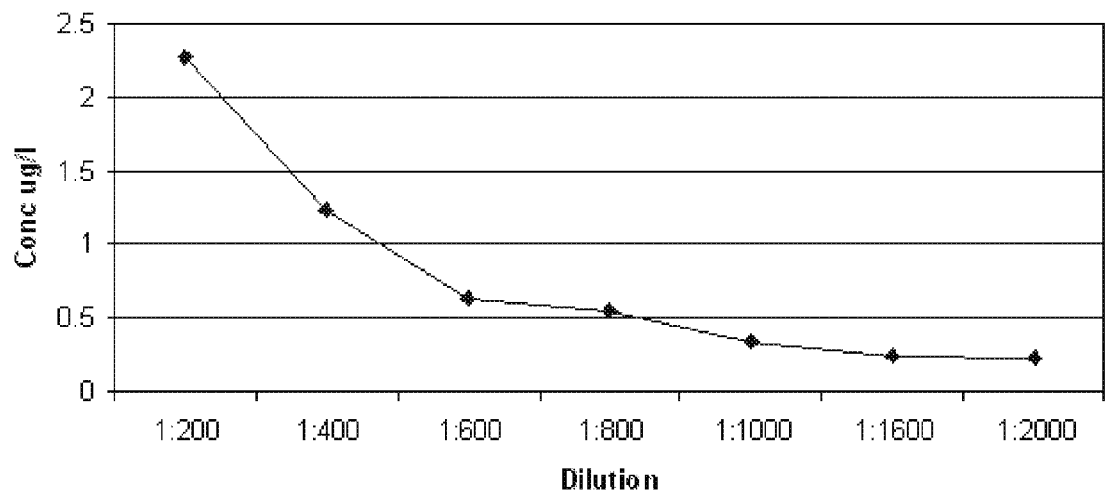
FIG. 15A shows serial dilution of supernatant of mouse beta-islet cells cultivated for 120 hours in a protein-free medium (XOM) supplemented with D-glucose.
Figure 15B:
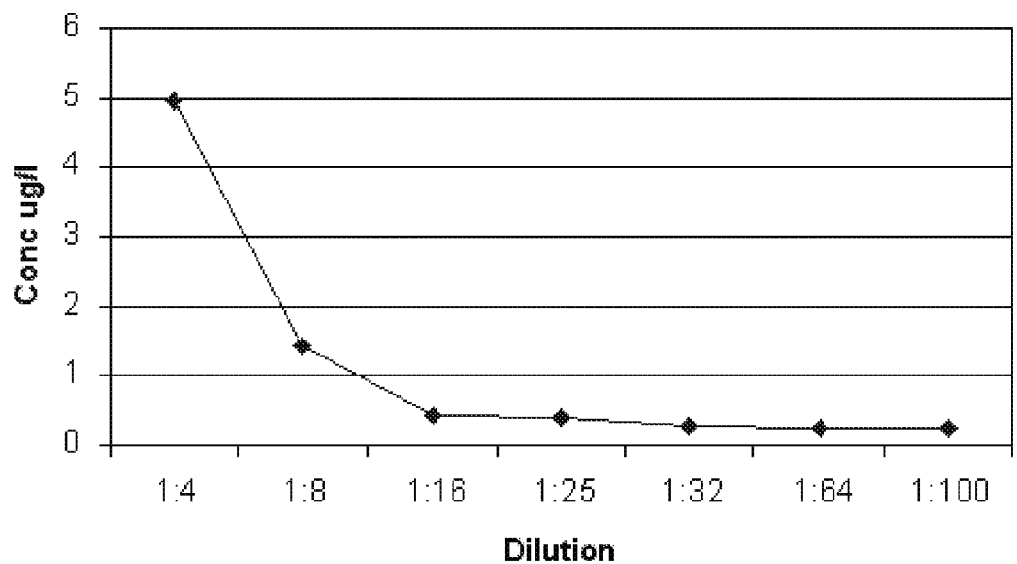
FIG. 15B shows serial dilution of supernatant of rat beta-islet cells cultivated for 120 hours in a protein-free medium (XOM) supplemented with D-glucose.
Figure 16:
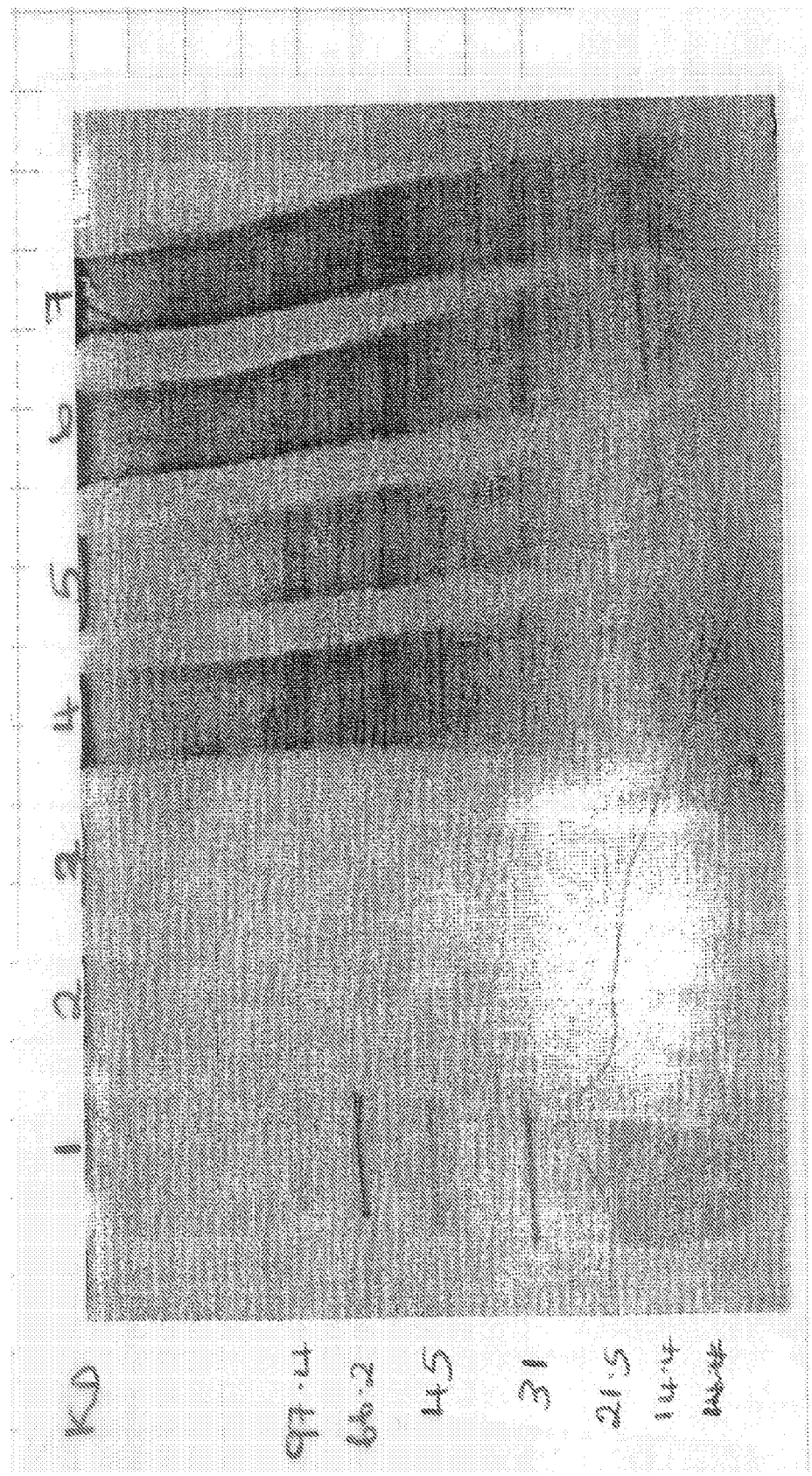
FIG. 16 shows an SDS-PAGE and silver staining of proteins released by rodent beta-islet cells into a protein-free medium (XOM) supplemented with glucose (GFXOM). Lanes 1: MW standards, 2: GFXOM, 3: PBS-used for dialysis, 4: Mouse 120 hours (no dialysis, 18 μg), 5: Mouse (dialysed, 18 μg), 6: Rat 120 hours (no dialysis, 18 μg), 7: Rat 120 hours (dialysed, 18 μg). Rodent beta-islet cells (mouse and rat) were cultivated in a protein-free medium (XOM) supplemented with D-glucose (GFXOM) for 120 hours. Aliquots of supernatants pre- and post-dialysis were run on SDS-PAGE and the gel silver stained to demonstrate proteins.

An ALPCO Diagnostics ELISA kit Lot #8194 that measures free insulin was purchased and the concentration of the putative insulin in various supernatants determined. The results of the rat and mouse adherent cell cultures are shown in FIGS. 14A and 14B and are indicative of the presence of free insulin in the medium. A dilution curve using the 120 hour sample from the adherent cell cultures show a measurable range of the ELISA to occur between (0.5 and 2.4 µg/1). See FIGS. 15 and 16.

In order to demonstrate the purity of the proteins secreted by the beta-islet cells into the medium, aliquots of the following media or supernatants (lane 1: MW standards; lane 2: GFXOM; lane 3: PBS-used for dialysis; lane 4: Mouse 120 hours (no dialysis, 18 µg); lane 5: Mouse (dialysed, 18 µg); lane 6: Rat 120 hours (no dialysis, 18 µg); lane 7: Rat 120 hours (dialysed, 18 µg) were prepared. There are no protein bands discernible in lane 2 (GFXOM) and lane 3 (dialysis fluid). However, the proteins secreted into GFXOM by both mouse and rat beta-islet cells are seen in the dialyzed and non-dialyzed supernatants. See FIG. 16. Rodent beta-islet cells (mouse and rat) were cultivated in a protein-free medium, GFXOM (XOM supplemented with D-glucose) for 120 hours. Aliquots of supernatants pre- and post-dialysis were run on SDS-PAGE and the gel silver stained to demonstrate proteins secreted into the medium. The identity and physiological activity of the secreted proteins may be readily established using methods known in the art. Therefore, the present invention provides methods for obtaining commercially viable amounts of cellular products from cells in a high degree of purity.

Therefore, the present invention provides a method of maintaining or modulating water homeostasis in a cell or a tissue ex vivo comprising cultivating the cell or the tissue in a protein free medium containing an oncotic agent. In some embodiments, the oncotic agent is sucrose, ficoll, sorbitol or D, xylose. In some embodiments, the protein free medium comprises a basic cell culture medium. There are several suitable basic cell culture media known in the art, including Minimal Essential Medium (MEM), Hams, Dubelco, RPMI-1640, Iscove, and the like. In some embodiments, the protein free medium is formulated with sucrose (SUM), ficoll (FIM), sorbitol (SOM), xylose (XOM), or xylose fortified with glucose (GFXOM).

In some embodiments, the present invention provides a method of obtaining a cellular product from a cell or a tissue comprising cultivating the cell or the tissue in a protein free medium containing an oncotic agent. In some embodiments, the oncotic agent is sucrose, ficoll, sorbitol or xylose. In some embodiments, the protein free medium comprises a basic cell culture medium. There are several suitable basic cell culture media known in the art, including Minimal Essential Medium (MEM), Hams, Dubelco, RPMI-1640, Iscove, and the like. In some embodiments, the protein free medium is SUM, FIM, SOM, XOM, or GFXOM. In some embodiments, the cellular product is secreted by the cell into the medium. It is noted, however, that in some embodiments the cellular product is not secreted into the medium, but may be obtained using methods known in the art. In some embodiments, the cellular product is a protein, a peptide, a nucleic acid molecule, a compound, a lipid, a glycolipid, a carbohydrate, and the like, or a combination thereof. The cellular product may be a recombinant cellular product. In some embodiments, the cell is a hybridoma, a beta-islet cell, a lymphocyte, a monocyte, a fibroblast, stem cell, an endothelial cell, or the like. The cell may be normal or abnormal, native or genetically engineered, obtained from a biopsy or a cell line from a repository. In some embodiments, the tissue is pancreatic tissue.

In some embodiments, the present invention provides a method of cultivating, propagating, preserving or storing an organism, a cell or a tissue comprising placing the organism, the cell or the tissue in a protein free medium containing an oncotic agent. In some embodiments, the organism is a barophylic organism. In some embodiments the barophylic organism is propagated at atmospheric pressure employing an oncotic agent to simulate hydrostatic pressure.

The following examples are intended to illustrate but not to limit the invention.

Example 1

Sera Preparation

Serum was collected from human patients who were admitted to clinics in Brazil, Italy, North Africa, Nepal and Walter Reed Army Medical Center and who had either splenic aspirates or skin biopsies from lesions that tested positive for *Leishmania* parasites by culture and microscopy. In total, 129 visceral (Italy, Brazil, North Africa, and Nepal) and 143 cutaneous (Brazil) leishmaniasis patients (136—*L. braziliensis*-infected, and 7 *L. panamensis*-infected) with controls were tested.

Human negative controls were from 12 non-endemic area normal patients with no documented infection or exposure to *Leishmania* parasites. In addition to the human manifestations assayed, sera from 42 Brazilian dogs with a clinical diagnosis for canine leishmaniasis were tested against positive control sera from a commercial source (Bordier Affinity Products, S. A., Crissier, Switzerland) and 10 negative controls from a pathogen-free, canine research colony (College of Veterinary Medicine, North Carolina State University, Raleigh, N.C., USA).

Example 2

Antigen Preparation

The *Leishmania* soluble antigen (exo-antigen) preparation was made by cultivating *Leishmania* promastigotes in normal supplemented media (RPMI, MEM plus FBS) at 26° C. until the culture reached mid-log phase at a density of about $10^9$ cells/ml. Then the cells were pelleted and washed 6 times in a defined, protein-free medium such as XOM available from GIBCO BRL, formula number 96-0051DJ, RPMI Medium 1640 comprising D, xylose at 0.076 mM, Hepes buffer at 25 mM, L-glutamine, and sodium bicarbonate at 30 mM without phenol red.

The cells were then resuspended in protein-free medium such as XOM to a final density of $10^8$ promastigotes/ml and incubated at 26° C. in a roller bottle with 0.01% Tween 80 (Sigma Chemical Co., St. Louis, Mo.) for 72 hours. The cells were pelleted by centrifugation at 9,000×g for 30 minutes and the supernatant was collected. The relative protein concentration of the soluble antigens was estimated by measuring the optical density at 280 nm. The antigen may be stored at 4° C.

Example 3

Antibody and Conjugate Production

The *leishmania* soluble antigen preparation produced by the method explained in Example 2 was used without an adjuvant to immunize rabbits. The antiserum was pooled and affinity-purified on a Protein A column containing the antigen preparation of Example 2 above. Fractions of the polyclonal antibody (PAb) were conjugated with an appropriate reporter system such as horseradish peroxidase, fluorescein and colloidal gold. These tagged antibodies may then be used in antigen-detection immunoassays such as ELISA, histochemical stain and dipstick test formats. These test formats may be used to detect parasite antigens in tissues and body fluids of mammalian hosts and vectors.

Figure 7:
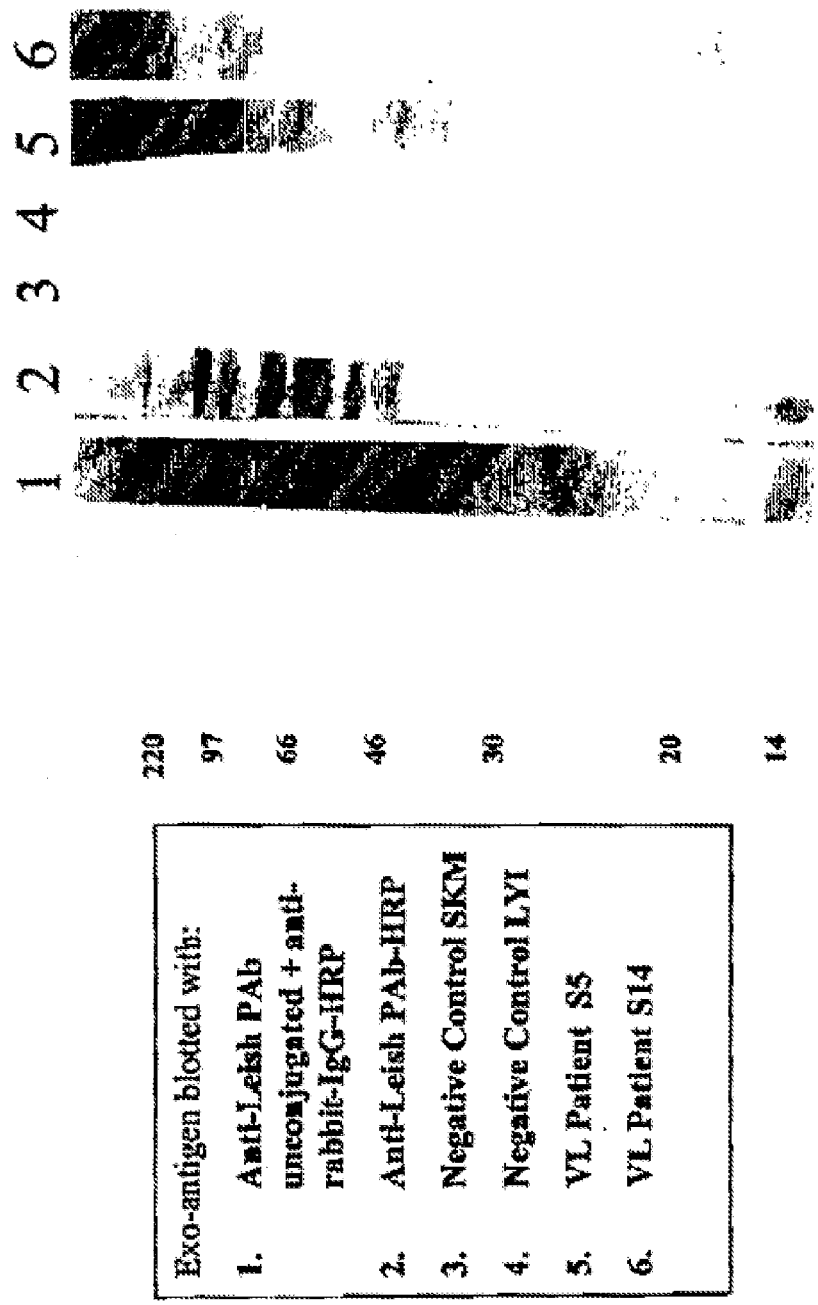
FIG. 7 of U.S. patent application Ser. No. 10/173,586 is incorporated herein and is a Western Blot illustrating the striking rabbit pattern (lanes 1 and 2) similar to that of the kala azar patients pattern (lanes 5 and 6).
Figure 8:
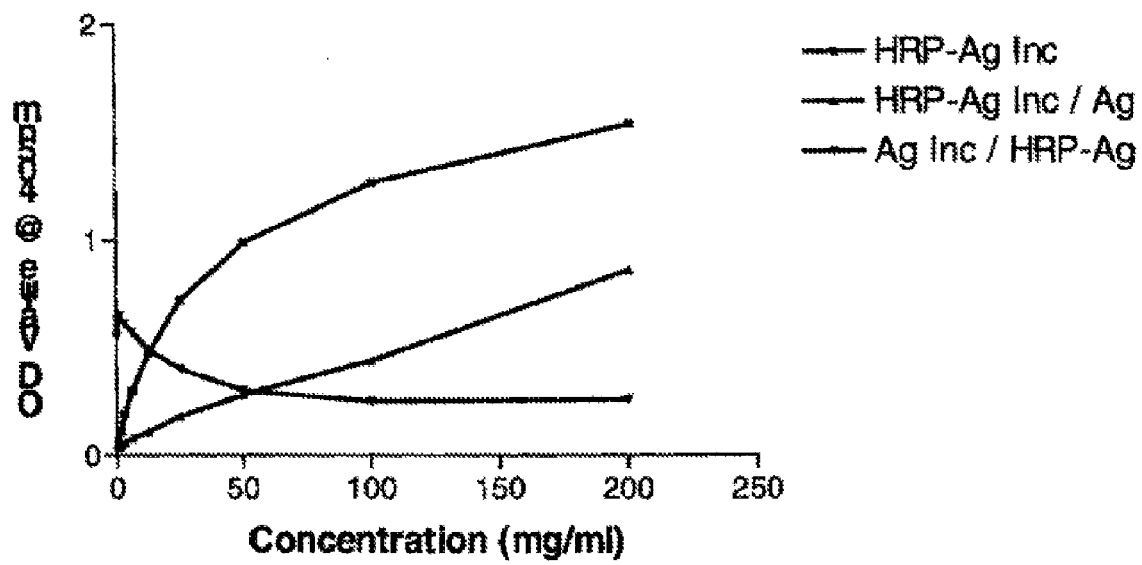
FIG. 8 is a graph illustrating the specific activity of the competitive Ag-capture ELISA while using different antigen and HRP-labeled antigen conditions.
Figure 9:
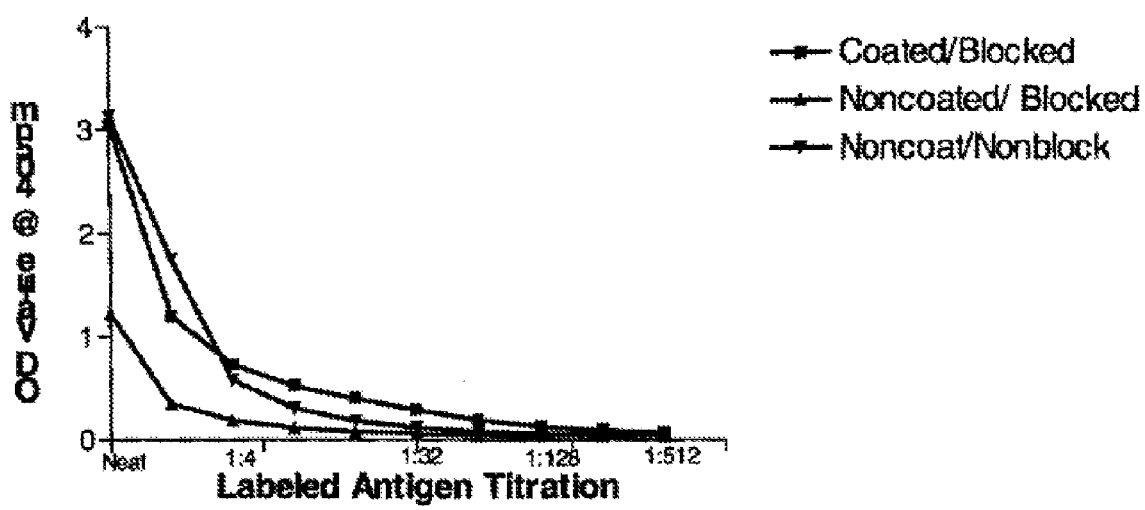
FIG. 9 is a graph illustrating the specific activity of the competitive Ag-capture ELISA while titrating labeled antigen under different coating and blocking conditions.

The rabbit anti-*leishmania* polyclonal antibody preparation demonstrated high affinity and avidity for the immunogens used to immunize the rabbits. The PAb produced a very striking Western Blot pattern similar to that of kala azar patients. See FIG. 7 of U.S. patent application Ser. No. 10/173,586, which is herein incorporated by reference.

It is appreciated that the present invention also encompasses monoclonal antibodies against *leishmania* soluble antigens, hybridomas producing such, and methods of making and using thereof. Thus, monoclonal antibodies against *leishmania* soluble antigens may be used in the assays described herein. The monoclonal antibodies may be made by standard methods known in the art.

Example 4

Antibody-Capture Enzyme-Linked Immunosorbent Assay

Generally, in the solid phase enzyme immunoassay for *Leishmania*, soluble antigens of the *Leishmania* promastigotes were coated on the inner surface of a test well which serve to bind specific antibody from a sample. Peroxidase conjugated antibody to anti-human IgG was added and reacted with bound antibody. A chromogenic substrate, such as horseradish peroxidase, for peroxidase was added. If antibody to *Leishmania* was present, there was a reaction that resulted in the development of color. Other fluorescent, chemiluminescent and chromogenic agents may be used with appropriate enzymes and substrates.

Plate sensitization was affected by coating a polystyrene, 96-well microtitre plates (Immulon 4, Dynatech Laboratories, Chantilly, Va.) with 100 µl of the respective exo-antigen solution (5 µg protein per well). *L. donovani* (Walter Reed reference strain 130, clone E) exo-antigen was used to sensitize plates for visceral and canine leishmaniasis samples, and *L. mexicana* (ATCC strain 50157) exo-antigen was used to sensitize plates for cutaneous leishmaniasis samples. Positive and negative controls were diluted at the same ratio as the sample. The dilutions were then placed in the wells of the microtitre plate. The samples were covered and incubated for 1 hour at room temperature in a humid environment.

Each plate was then blocked with 1.0% casein (Sigma Chemical Co., St. Louis, Mo.) in PBS for one hour at room temperature. The blocking buffer was removed by aspiration and the serum samples (100 µl of 1:1000 dilution) and appropriate controls were added to the microtiter plate and the plate was incubated at 26° C. for 40 minutes. The plate was washed with 0.05% PBS-Tween-20 (PBS-Tween) buffer four times. Preferably, an automatic plate/strip washer is used. The well contents were shaken out at the end of the final wash. Then goat anti-human IgG (whole molecule) conjugated with horseradish peroxidase (Kirkegaard & Perry Laboratories Inc., Gaithersburg, Md.) was added at 1:5000 dilution and then the plate was incubated at 26° C. for an hour in a humid environment.

The plate was then washed four times with PBS-Tween buffer and 100 µl of TMB substrate (KPL. Inc., Gaithersburg, Md.) was added to each well. The plate was incubated for about 15 minutes in the dark. The optical density (OD) was periodically read at 650 nm wavelength in an ELISA plate reader (Molecular Devices, Menlo Park, Calif.) until the OD value of a reference positive control (S5, Kala azar patient, Nepal) reached 0.8. At this point 100 µl of a stop solution (0.1M phosphoric acid) was applied to each well and the final OD reading was taken immediately at 450 nm. Preferably, a dual beam ELISA reader is used.

A reference positive serum was used in all plates, and only interassay variation of less than 10% was accepted. The lower limit of positivity (cut off) was determined by the mean of the negative controls subset +3 standard deviations.

A. Visceral *Leishmaniasis*.

Generally, for the test results to be accepted for visceral *leishmania*, the negative control must have an OD reading under 0.15 and the positive control must be over 0.8 at 650 nm. If the controls do not satisfy this criteria, the test should be repeated. Samples yielding absorbance values under 0.2 are negative and samples above 0.2 but below 0.3 may contain antibody but the amount is lower than the generally accepted significant level. It is noted that one may designate a more stringent or less stringent range for determining the absorbance levels that are indicative of exposure to leishmaniasis antigen. Samples giving absorbency values above 0.3 contain higher levels of antibody that are generally considered to be at or above the significant level.

*L. donovani* WR0130E (ATCC strain 30503) exo-antigen was used as the material to coat the microtitre plate. The negative control sera subset gave a negative cutoff score of about 0.225 for the IgG assay. With respect to specific IgG, all 129 clinically confirmed positive VL patient sera gave OD readings above the negative cutoff (100% sensitivity). When measuring IgM, the negative control sera tested gave a negative cutoff score of about 0.310. The sensitivity for this assay was 94.57% (122/129 positive).

B. Cutaneous *Leishmaniasis*.

Generally, for the test results to be accepted for cutaneous leishmaniasis, the negative control must have an OD reading under 0.3 and the positive control must be over 0.8 at 650 nm. If the controls do not satisfy these criteria, the test should be repeated. Samples yielding absorbance values under 0.3 are negative and samples above 0.3 but below 0.3 may contain antibody but the amount is lower than the generally accepted significant level. Again it is noted that one may designate a more stringent or less stringent range for determining the absorbance levels that are indicative of exposure to leishmaniasis antigen. Samples giving absorbance values above 0.3 contain higher levels of antibody that are generally considered to be at or above the significant level.

Figure 3:
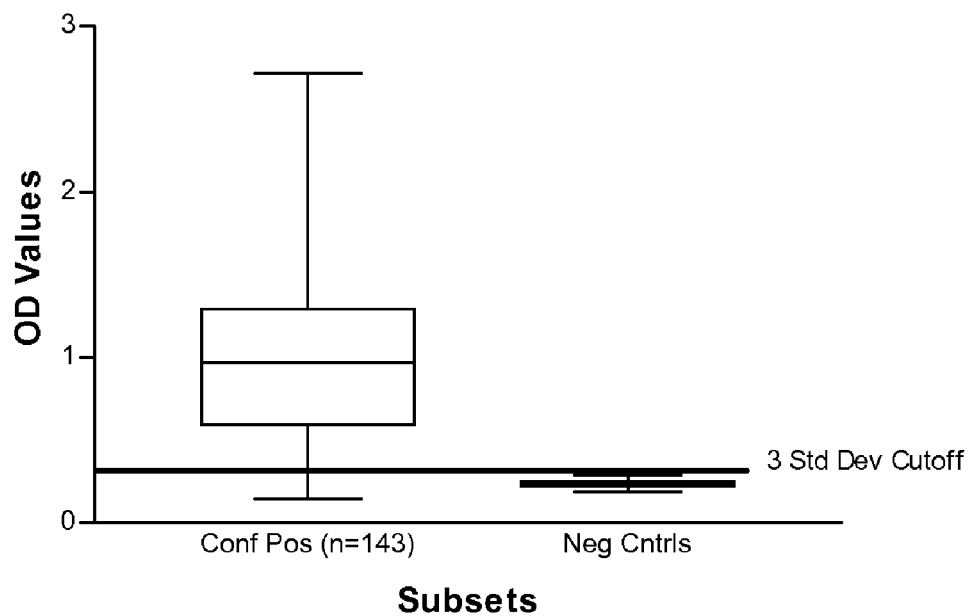
FIG. 3 is a boxplot illustrating specific IgG antibody levels measured in CL patient sera samples.
Figure 4:
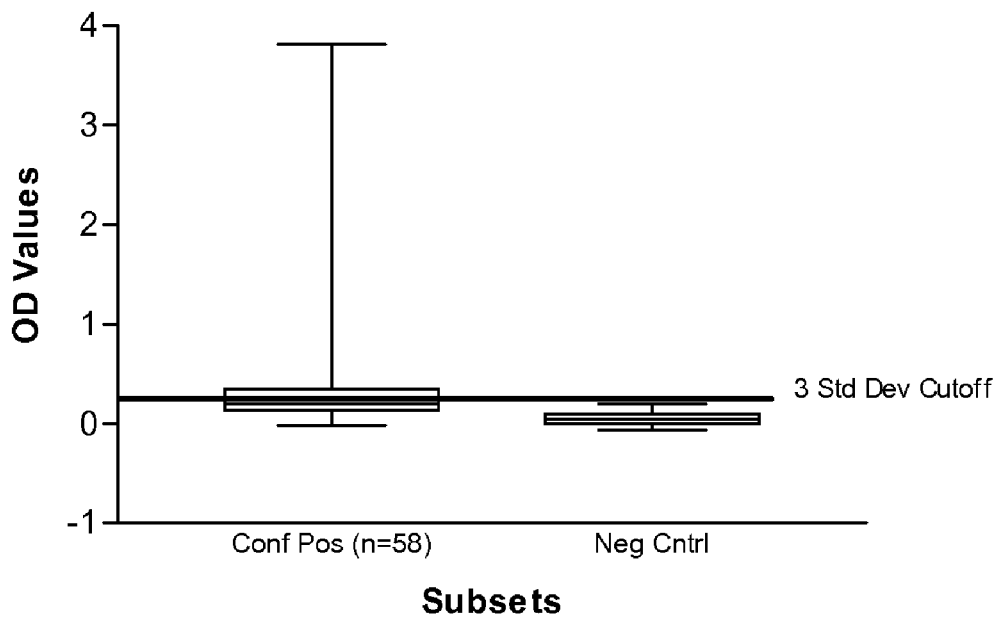
FIG. 4 is a boxplot depicting specific IgM antibody levels measured in the same samples.

*L. mexicana* exo-antigen (ATCC strain 50157) was used as the material to coat the microtiter plate. The negative control sera subset gave a negative cutoff score of approximately 0.3 for the IgG assay. The boxplot in FIG. 3 illustrates specific IgG antibody levels measured in CL patient sera samples. With respect to specific IgG, 132/143 clinically confirmed positive CL patient sera gave OD readings above the negative cutoff (92.31% sensitivity). FIG. 4 is a boxplot depicting specific IgM antibody levels measured in the same samples. When measuring IgM, the negative control sera tested gave a negative cutoff score of approximately 0.15. Only a few samples (n=6) were dramatically above the negative cutoff score, the majority of values for positive samples at or near the median value of the negative control subset. This assay failed to consistently detect specific IgM in CL patient sera samples (37.9%; 22/58 positive).

C. Canine *Leishmaniasis*.

Figure 5:
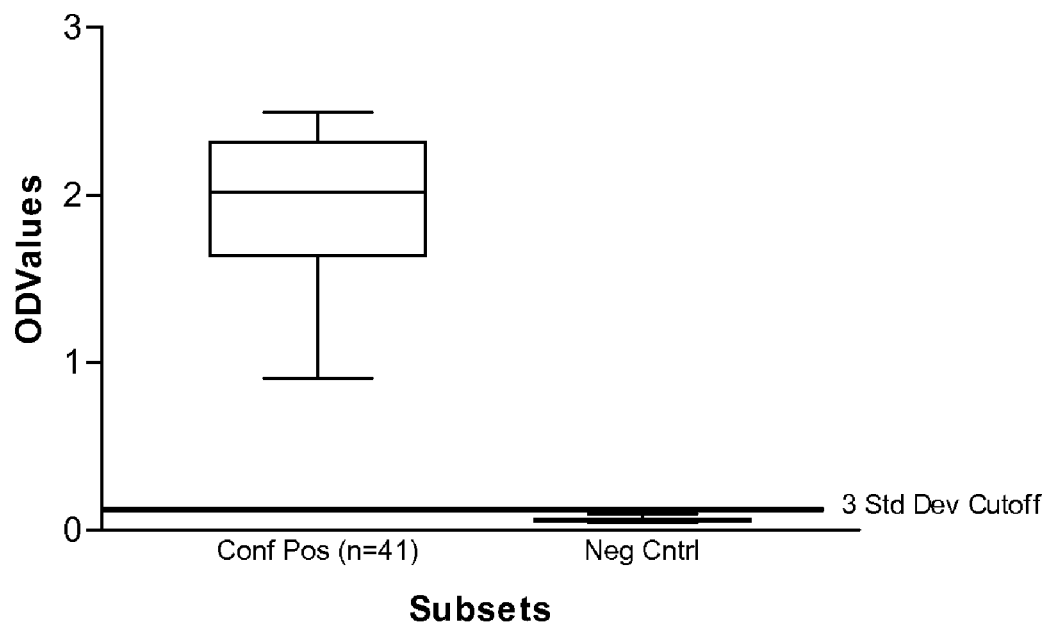
FIG. 5 shows specific IgG antibody levels measured in canine leishmaniasis sera samples.
Figure 6:
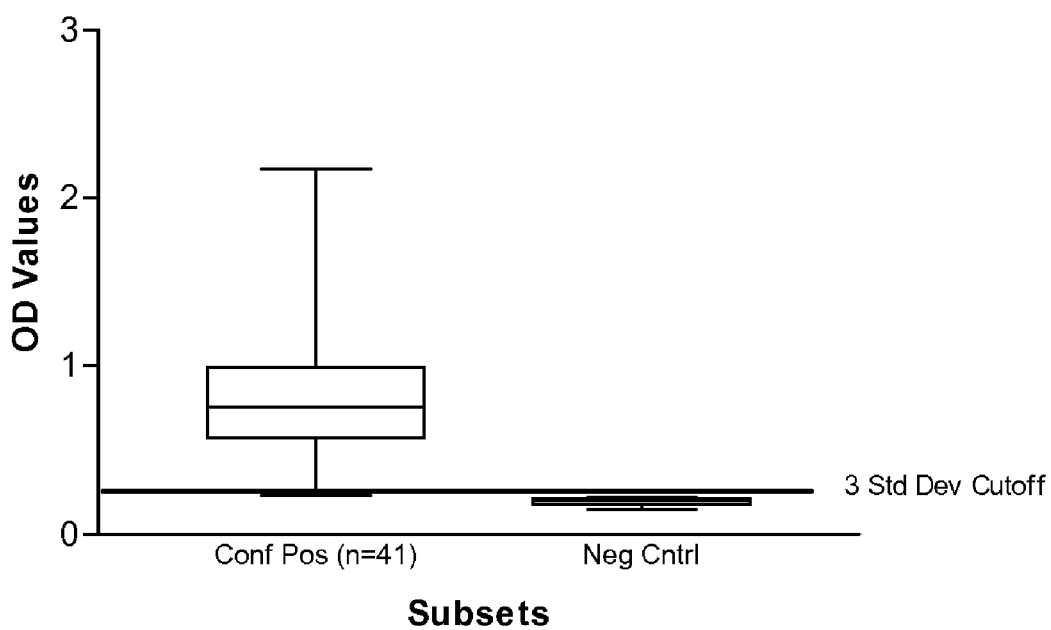
FIG. 6 is a boxplot that displays specific IgM antibody levels measured in the same samples.

*L. donovani* WR0130E (ATCC strain 30503) exo-antigen was the material used to coat the microtitre plate. The negative control sera subset gave a negative cutoff score of an OD reading of about 0.1 at 650 nm for the IgG assay. FIG. 5 shows specific IgG antibody levels measured in canine leishmaniasis sera samples. With respect to specific IgG, all 41 clinically confirmed positive canine leishmaniasis sera samples gave OD readings above the negative cutoff (100% sensitivity). Note the relatively large degree of separation between the positive and negative control subsets. The boxplot in FIG. 6 displays specific IgM antibody levels measured in the same samples. When measuring IgM, the negative control sera tested gave a negative cutoff score of approximately 0.25. The sensitivity for this assay was 97.56% (40/41).

SDS-PAGE and Western Blot analysis confirmed the ELISA results for both VL and CL patients, canine and all negative controls. Mini-Protean II (Bio-Rad, Hercules, Calif.) was used for SDS-PAGE. Each antigen preparation was boiled for 5 minutes in sample buffer without a reducing agent and was immediately subjected to electrophoresis on 4% stacking, 12.5% separating bis-acrylamide gels. A wide-range molecular mass marker (Bio-Rad, Hercules, Calif.) was used. An antigen load of 120 µg of protein was used in each mini-gel. The gels were run at 100 V of constant voltage for 1.5 hours in Tris-glycine-SDS buffer (pH 8.3).

Protein bands from the gel were transferred to nitrocellulose. Antigens from the SDS-polyacrylamide gels were electroblotted onto 0.45 µm pore size nitrocellulose membranes (Bio-Rad, Hercules, Calif.) with standard transfer buffer (0.02 M Tris, 0.15 M glycine, 0.1% SDS, 20% methanol) and 250 mA of constant current for 1 hour at 4° C. Following the blotting, portions of the membranes containing the protein markers were stained with 0.5% Amido black for 5 minutes and were destained in distilled water—glacial acetic acid solution. The membranes were immediately blocked with a 2% skim milk TTBS (100 mM Tris, 0.9% NaCl, 0.1% Tween 20) solution and kept refrigerated until use.

Detection of antibodies from subject sera bound to the antigens of the Western blot was done with an avidin-biotin-alkaline phosphatase system by methods standard in the art. Strips 4 mm wide were cut from previously blotted and blocked membranes. These strips were incubated with diluted sera (1:3,200 in TTBS) for 30 minutes at room temperature with constant agitation. After incubation with the primary antibody, the strips were washed 4 times for 10 minutes each time with TTBS. After the last wash, biotinylated, anti-human immunoglobulin G was added and the mixture was incubated for 30 minutes under the same conditions as described above. Preformed avidin-biotin-alkaline phosphatase complex was added. The mixture was then incubated under the same conditions as above. The membranes were developed with a BCIP/NBT substrate (Kirkegaard & Perry Laboratories, Gaithersburg, Md.) for 5 minutes. The reaction was stopped by rinsing the strips with distilled water and then adding PBS-EDTA (20mM).

Example 5

Antigen-Capture Enzyme-Linked Immunosorbent Assay

A. General Antigen-Capture ELISA.

An antigen-capture ELISA ("sandwich" ELISA) format based on the same soluble antigens and their complementary antibodies was developed to detect active infection in vertebrate hosts and sand fly vectors.

The capture polyclonal antibody was adsorbed to the wells of a microtiter plate. After the capture polyclonal antibodies were bound to the plate, the well contents were aspirated and the remaining active binding sites on the plates were blocked with blocking buffer. A sample such as patient sera, urine, or ground sand flies was then tested. Test samples were appropriately diluted with blocking buffer and an aliquot was tested. Sand flies to be tested were ground in blocking buffer with Nonidet P-40 (ELISA grade Sigma casein, bovine milk) and an aliquot was tested. Positive and negative controls were also added.

If parasite antigen was present it formed antigen-antibody complexes with the polyclonal sera used to coat the plate. After a 2-hour incubation, the sample was aspirated and the wells were washed. The peroxidase-linked polyclonal sera were then added to the wells, thereby completing the formation of the sandwich. Other chromogenic agents such as colloidal gold and FITC may be used with their corresponding substrates.

After 1 hour, the well contents were aspirated, the plate was washed and a clear peroxidase substrate solution from Kirkegaard & Perry Laboratories (Gaithersburg, Md.) was added. As the peroxidase enzyme reacted with the substrate a dark product was formed, which the intensity of its color was relative to the amount of circulating antigen present in the test sample. Quantitative results were obtained by making an endpoint determination a few minutes after the substrate has been added by measuring the optical density of the well contents at 450 nm with an ELSIA plate reader. However, qualitative results may be read visually in the field. ELISA positive samples may be retested to confirm positives and to estimate the amount of circulating antigen per sample.

Recently, the antigen-specific, conjugated polyclonal antibodies were used in combination with unconjugated PAb and monoclonal antibodies (MAb) specific for leishmanial Secretory Acid Phosphatases (S-cAcP) to develop a simple antigen-capture assay. The sensitivity of this assay was tested with serial dilutions of the antigen preparation prepared from the method explained above. Specific activity was recorded with the use of an HRP conjugate at a 1:32,000 dilution. The level of sensitivity in measuring these antigens with PAb was 400 ng/ml.

B. Rapid Wicking Assay.

A rapid wicking assay, based on the dual "sandwich" ELISA, was developed. The assay is conducted by placing a dipstick impregnated with immobilized polyclonal antibodies from rabbits immunized with the soluble antigen (Cellabs Pty, Ltd. Sydney, Australia) into a test solution. When soluble leishmanial antigen is present in the solution, it binds to a specific antibody with a gold sol particle label. As the antigen-antibody-gold complexes migrate through a test zone on the dipstick comprising immobilized polyclonal antibodies from rabbits immunized with the soluble antigen (Cellabs Pty, Ltd. Sydney, Australia), they bind to the corresponding immobilized antibodies to form a "sandwich". The unbound dye complexes migrate out of the test zone and can be captured later in a control zone. A reddish-purple line develops in the specific area of the test zone when antigen is present. A control line in the control zone should develop provided that the test was conducted correctly.

The test zone comprises immobilized polyclonal antibodies from rabbits immunized with the soluble antigen (Cellabs Pty, Ltd. Sydney, Australia). The control zone comprises antibodies to immobilized polyclonal antibodies from rabbits immunized with the soluble antigen (Cellabs Pty, Ltd. Sydney, Australia). Monoclonal antibodies against the soluble antigen may be used.

The test samples may be sand flies or other organisms comprising *leishmania* parasites ground up in a solution such as PBS with 0.5% casein. Alternatively the test samples may be blood, serum, urine, mucus, tears, stool or the like, obtained from a subject. When the test sample is urine, it is preferably undiluted.

Example 6

In vitro Direct Immunofluorescence Test

Fluorescein-labeled polyclonal antibodies raised against specific antigens of *Leishmania* parasites may be used in an in vitro direct immunofluorescence assay. The labeled antibody binds specifically to the antigens present on the surface of the parasite which can be detected in a variety of smears such as vector specimen, in vitro culture material and patient biopsy smears.

Smears were prepared on glass slides and fixed with methanol. Unbound antibodies were removed by washing. When viewed under a fluorescence microscope, *Leishmania* parasites were seen as bright apple-green organisms characteristic to their life cycle stages contrasted with the reddish brown color of counterstained material. Promastigotes in the vectors or in culture were detected by their characteristic long and slender body (about 20 µm in length) with an anterior flagellum. Amastigotes present in clinical samples were detected by their characteristic round or oval shape measuring about 2-5 µm in diameter.

Generally, sample smears were prepared on slides marked with wells or on plain glass slides. Suitable smears had adequate specimen and were moderately thin. For sample smears prepared on a single well slide, an adequate amount of fluorescein-labeled purified polyclonal antibody diluted in a protein stabilized buffer solution (pH 7.4) with Evans Blue as a counter stain and 0.1% w/v sodium azide was added to the fixed sample smear and positive control.

For smears prepared on plain glass slides, after drying, the smear was pretreated by dipping the slide in a Coplin jar containing 0.1% sodium deoxycholate prepared in 0.85% NaCL for 5-10 minutes. The smear was air-dried. Then an adequate amount of fluorescein-labeled purified polyclonal antibody diluted in a protein stabilized buffer solution (pH 7.4) with Evans Blue as a counter stain and 0.1% w/v sodium azide was added to the fixed sample smear and positive control.

The slides were incubated at 37° C. in a moist chamber for 30 minutes in the dark. Then the slides were rinsed in a saline bath for about 2-5 minutes. The slides were allowed to air dry and then mounted with coverslips. With a fluorescence microscope under oil immersion, the slides were read.

This test format was found to be very sensitive to detecting amastigotes in infected patient tissues from subjects with cutaneous leishmaniasis infected with *L. brasiliensis* and splenic aspirates from subject with visceral leishmaniasis infected with *L. donovani*. It may be used to highlight surface antigens and cellular structure in cultured promastigotes. Preliminary results from gene cloning experiments with the *L. donovani* clone used to produce the exo-antigen indicate that one of the major immunogens in the sensitization of the rabbits used to generate the PAb is a major surface antigen.

Example 7

Competitive ELISA

Microtiter plates were coated with the anti-*leishmania* PAb and blocked with 1% yeast extract. The exo-antigen was labeled with HRP. The resulting exo-antigen conjugate was mixed 1:1 with samples and applied to the plate and incubated overnight at 4° C. The plate was washed 3 times with PBS and a substrate, ABTS, was applied. The optical density of the samples were read at 405 nm.

The competitive ELISA format worked to indirectly detect free antigen in samples. There was a correlation between increasing amounts of antigen in the samples and reduced optical density values. Further experiments were conducted to demonstrate that this relationship remained intact when varying the amount of the labeled or unlabeled antigen in the test sample and to demonstrate the importance of coating and blocking wells prior to sample incubations. See FIGS. 8 and 9.

Example 8

Assay Optimization

The antibody detection ELISA may be optimized for diagnosis of visceral and cutaneous leishmaniasis. For example, for assay optimization for VL, the antigens released by *L. donovani* promastigotes (WHO Reference Strain 065) in vitro at 26° C. for 72 hours into serum-free and protein-free medium were obtained as described in *Martin* et al., (1998) and used. The soluble antigens were separated by SDS-PAGE using 4-15% Novex gradient gels (Novex, San Diego, Calif.). The proteins were visualized by colloidal Coomassie blue G-250 and silverstaining The molecular weights of the secreted antigens were estimated with the reference to a prestained standard (Novex, San Diego, Calif.).

Titration and checker-board analyses were performed to optimize the assay protocol. Optimal results were obtained when antigen (50 μg/ml) was coated with PBS-methyl glyoxal buffer and the wells were blocked with 0.5% casein. It was found that a serum dilution of 1:500 in antigen-coated wells blocked with 0.5% casein generated lowest absorbance with negative control sera and higher absorbance with positive sera, sera from well-characterized, culture positive case subjects (used as reference positives).

An equal number of sera from North American naives with no travel history to *leishmania* endemic areas were used as reference negatives, negative controls or negative sera. These sera samples were used as reference samples to optimize the assay. The reference sera were not pooled and were used as individual data points. After optimizing the assay, individual sera samples obtained from endemic areas of N. Africa were screened and used to show assay performance in terms of specificity and sensitivity.

Two ELISA plates, Greiner (Greiner Labortecnik ELISA plate Cat #705071) and Labsystem (Labsystem combiplate breakable 8 Cat #95029400), were evaluated.

The following four different coating buffers (a) 0.2M carbonate/bicarbonate buffer pH 9.6, (b) 0.01M phosphate buffer ($PO_4$) pH 7.2, (c) blank culture medium (serum-free) pH 7.2, and (d) 0.1M phosphate buffered saline (pH 7.2)+1% methyl glyoxal were tested for their ability to immobilize the antigen onto the solid phase ELISA wells.

Gelatin ranging in concentration from 0.1 to 0.4% solution and 0.5% casein were tested. BSA and other routinely employed blocking agents were not tested because of non-specific binding noted in previous experiments.

PBS/T and PBS/T+0.2M NaCl were used as the washing buffers. An automatic plate washer (Denley Well Wash 04) with 4 cycle wash in each step was used to wash the ELISA wells. In most of the assays the wash buffer was used as the diluent for sera as well as the conjugated detector antibody.

Two anti-human IgG conjugated to HRP (HRP conjugate) were tested. A goat anti-human IgG-HRP (Kirkegaard & Perry Laboratories, Gaithersburg, Md.), a polyclonal conjugate (PAb conjugate), and a mouse anti-human IgG-HRP (Cellabs, Brookvale, Australia), (MAb conjugate).

All steps of the ELISA were performed at room temperature. The S/N ratio, the differential absorbance between the negative sample versus the test or positive sera sample, was used to quantify the specific antigen and antibody reactions. An anti-human monoclonal antibody conjugated with HRP (MAb conjugate) outperformed a commercially available anti-human polyclonal antibody conjugate (PAb conjugate) (Cellabs Pty, Ltd. Sidney, Australia). The MAb conjugate gave minimal background reactions with endemic sera.

Generally, the wells of an ELISA plate were coated with 50 μg/mL of the soluble antigens released by *L. donovani* promastigotes in serum-free and protein-free medium mixed in PBS-methyl-glyoxal overnight. After removing the antigen, the wells were blocked with 0.5% casein for 1 hour at room temperature. Test sera along with positive and negative control sera diluted 1:500 in PBS/T, were reacted for 1 hour at room temperature. After washing the plate with PBS/T, the wells were reacted with an HRP-conjugated anti-human antibody, the detector antibody, for 40 minutes at room temperature. The plates were washed and specific binding of antigens on the solid phase and the specific antibodies present in the test sera were measured indirectly by the binding of HRP labeled detector antibody which was further detected by using TMB+$H_2O_2$ as a chromogenic substrate.

TMB solution A and B (KPL, Gaithersburg, Md.) were mixed in equal parts 5-10 minutes before and transferred an aliquot of 100 μl to each well as per the guidelines provided by the manufacturer. During the developmental phase of the assay, the color intensity of positive sera wells was monitored (absorbance OD of 620 nm) and stop solution was added when those wells reached an OD of 0.450. In the final optimized assay, the incubation time with substrate was fixed at 25 minutes.

After adding the stop solution (1M Phosphoric acid prepared in distilled water) the contents were mixed and the plate was read at dual filter (450/620 nm) using a plate reader (Anthos LabTec Instruments 2001).

The raw data from the plate, i.e., absorbance at 450/620 nm, were plotted into histograms and graphs. The relative specific binding was quantified by the signal to noise (S/N) ratio which was calculated by dividing the mean absorbance, i.e., absorbance at 450/620 nm, of test sera with the mean absorbance of negative sera, and plotted. The S/N ratio was directly proportional to the specific antibody reactivity in ELISA. A batch of n=22 endemic sera from North Africa were evaluated and resulted with 100% specificity and sensitivity, 99.99% PPV (positive predictive values) and 95.45% NPV (negative predictive values).

The LabSystem plate did not perform well in this study. There was no discrimination between the positive and negative sera. There was a clear distinction between sera in the Greiner plate. It was found that the PBS+methyl glyoxal, phosphate buffer and culture medium respectively showed higher reactivity with positive sera and relatively less reactivity with negative sera. A higher S/N ratio was seen using sera at a 1:500 sera dilution. Phosphate buffer, culture medium and PBS-glyoxal gave higher S/N ratios. Therefore, the Greiner plate and PBS+methyl glyoxal were selected as ELISA plate and coating buffer respectively.

Using the Greiner ELISA plate and PBS+methyl glyoxal as the coating buffer for the test, positive and negative sera were used at 1:500 dilution. Two anti-human IgG-HRP conjugates were evaluated at 4 different dilutions. The PAb conjugate was found to be highly reactive with the negative sera indicating a high level of non-specific reaction. On the other hand, the same level of reactivity was observed in the blank and negative sera sample wells with the MAb conjugate. The reactivity with MAb conjugate appeared to be more specific with positive sera as evidenced by higher S/N ratios.

Negative and positive sera were reacted at 1:500 dilution and washed with two different wash solutions. MAb conjugate was used at 1:8000 dilution. Plates were read at 450/620 nm. Reactivity of blanks and negative sera were lower in wells washed with PBS/T+0.2M NaCl. The data indicated that PBS/T+0.2M NaCl was more effective in removing non-specific binding (nearly 45% reduction of non-specific signal 0.283 v. 0.114) and increasing the S/N ratio from 3.7 to 7.2. Despite its higher S/N ratio, 0.2M NaCl was left out of the final wash buffer because it formed a precipitate on standing.

Having selected the Greiner plate and PBS+glyoxal as the coating buffer, optimum levels of antigen and appropriate blocking reagents were investigated. Wells were coated with a series of antigen concentration from 1.25 µg/ml to 40 µg/ml. Two blocking reagents, 0.4% gelatin and 0.5% casein prepared in distilled water were evaluated. Positive and negative sera, diluted 1:500 in PBS/T, reacted in the Ag-coated and blocked wells for 1 hour at room temperature. Two conjugates, PAb and MAb-conjugates, diluted 1:4000 in PBS/T were added to wells and incubated for 30 minutes at room temperature. The color was developed for 25 minutes by adding the substrate and immediately read after addition of stopping solution. The reactivity was higher in blank and negative sera wells with PAb conjugate thereby reducing the differences between samples that resulted with a low S/N ratio. With the MAb conjugate, the absorbance of blank and negative sera wells was almost equal. There was a pattern in the reactivity relative to the antigen concentration. Wells reacted with the positive sera showed a gradual rise in absorbance dependent upon the antigen concentration. On the whole, MAb conjugate reactivity was relatively lower in control sample wells. The S/N ratios were higher with MAb conjugate when casein used for blocking MAb conjugate with casein blocking generated excellent S/N ratios, at 20 and 40 µg/ml antigen levels.

Experiments involving the relative kinetics of antibody reactivity at different sera dilutions provided a good discrimination at 1:500 dilution. This formed the basis for future assays.

After optimizing assay steps, the following protocol was followed for evaluating test sera samples of subjects from endemic areas. In short, the wells were coated with 50 µg/ml soluble antigen mixed in PBS-methyl-glyoxal buffer overnight and after removing the antigen, the wells were blocked with 0.5% casein for 1 hour at room temperature. Test serum along with control sera diluted 1:500 in PBS/T, was reacted for 1 hour at room temperature. After washing the plate in PBS/T, the wells were reacted with MAb conjugate at 1:8000 dilution for 40 minutes at room temperature and after washing, the TMB substrate was added and color development was allowed to proceed for 25 min and then stopped with the stop solution.

Absorbance was read at dual filter (450/620 nm) and the results were analyzed. A total of n=22 test clinical sera obtained from the endemic areas of North Africa were evaluated along with n=5 reference control negative sera.

SDS-PAGE analysis was conducted Coomassie staining showed several major bands with approximate molecular weights of 11, 30, 42, 50 and 161 kDa. In addition to these abundant bands, silver staining revealeed more distinct protein bands of approximately 6, 15, 17, 22, 58, and 107 kDa. This illustrates that the test contained a variety of protein antigens.

The cut-off value in the current assay was mean +3 SD of negative (n=5) sera (Mean 0.1304, SD=0.042), i.e., 0.278 which is rounded off to 0.300. Using an absorbance OD450/620 nm of 0.300 as the cut off, n=22 test sera from field were categorized as either positive or negative. With the exception of one sample, all were positive. The sensitivity, specificity, PPV and NPV were calculated. Thus, the sensitivity and specificity were both 100%, the PPV was 99.9% and NPV was 95.45%. The resultant S/N ratio of these samples suggests that the assay is highly sensitive and specific.

Clearly, one of ordinary skill in the art may further optimize the assays of the invention by changing various assay conditions by methods standard in the art.

To the extent necessary to understand or complete the disclosure of the present invention, all publications, patents, and patent applications mentioned herein are expressly incorporated by reference therein to the same extent as though each were individually so incorporated.

I claim:

1. A method of obtaining a cellular product from a cell or a tissue comprising cultivating the cell or the tissue in a protein free medium containing (a) an oncotic agent that balances the oncotic pressure across a semi-permeable cell membrane, and (b) at least one of the following ingredients: Hepes buffer, L-glutamine and sodium bicarbonate without phenol red.

2. The method of claim 1, wherein the cellular product is secreted by the cell into the protein free medium.

3. The method of claim 1, wherein the cell is a hybridoma, a beta-islet cell, a lymphocyte, a monocyte, a macrophage, a fibroblast, a stem cell, or an endothelial cell.

4. The method of claim 1, wherein the oncotic agent is sucrose, polysucrose, sorbitol or D-xylose.

5. The method of claim 1, wherein the protein free medium further comprises RPMI Medium 1640, Hepes buffer, L-glutamine, and sodium bicarbonate without phenol red.

6. The method of claim 1, wherein the protein free medium is RPMI Medium 1640 comprising D-xylose at 0.076 mM, Hepes buffer at 25 mM, L-glutamine, and sodium bicarbonate at 30 mM without phenol red.

7. The method of claim 1, wherein the protein free medium is RPMI Medium 1640 comprising D-xylose at 0.076 mM, Hepes buffer at 25 mM, L-glutamine, sodium bicarbonate at 30 mM without phenol red, and 300 mg/dl D-glucose.

8. The method of claim 1, wherein the protein free medium is RPMI Medium 1640 comprising D-sucrose at 0.076 mM, Hepes buffer at 25 mM, L-glutamine, sodium bicarbonate at 30 mM without phenol red, and 300 mg/dl D-glucose.

9. The method of claim 1, wherein the protein free medium is RPMI Medium 1640 comprising polysucrose at 0.076 mM, Hepes buffer at 25 mM, L-glutamine, sodium bicarbonate at 30 mM without phenol red, and 300 mg/dl D-glucose.

10. The method of claim 1, wherein the protein free medium is RPMI Medium 1640 comprising D-sorbitol at 0.076 mM, Hepes buffer at 25 mM, L-glutamine, sodium bicarbonate at 30 mM without phenol red, and 300 mg/dl D-glucose.

11. The method of claim 1, wherein the tissue is pancreatic, liver, heart, brain, or kidney tissue.

12. A method of cultivating, preserving or storing an organism, a cell, a tissue or organ comprising placing the organism, the cell, the tissue or organ in a protein free medium containing (a) an oncotic agent that balances the oncotic pressure across a semi-permeable cell membrane, and (b) at least one of the following ingredients: Hepes buffer, L-glutamine and sodium bicarbonate without phenol red.

13. The method of claim 12, wherein the organism is a barophylic cell or organism.

14. A method of obtaining a cellular product from a cell or a tissue comprising cultivating the cell or the tissue in a protein free medium containing an oncotic agent that balances the oncotic pressure across a semi-permeable cell membrane, RPMI Medium 1640, Hepes buffer, L-glutamine, and sodium bicarbonate without phenol red.

15. The method of claim 14, wherein the oncotic agent is sucrose, polysucrose, sorbitol or D-xylose.

16. The method of claim 15, wherein the oncotic agent is at 0.076 mM.

17. The method of claim 14, wherein the Hepes buffer is at 25 mM.

18. The method of claim 11, wherein the sodium bicarbonate is at 30 mM without phenol red.

19. The method of claim 14, wherein the protein free medium further comprises D-glucose.

20. The method of claim 12, wherein the protein free medium comprises D-xylose, RPMI Medium 1640, Hepes buffer, L-glutamine, and sodium bicarbonate without phenol red.

* * * * *